US 9,808,185 B2

(12) United States Patent
Arnold et al.

(10) Patent No.: US 9,808,185 B2
(45) Date of Patent: Nov. 7, 2017

(54) MOVEMENT MEASURE GENERATION IN A WEARABLE ELECTRONIC DEVICE

(71) Applicant: Fitbit, Inc., San Francisco, CA (US)

(72) Inventors: Jacob Antony Arnold, Fremont, CA (US); Subramaniam Venkatraman, Walnut Creek, CA (US)

(73) Assignee: Fitbit, Inc., San Francisco, CA (US)

( * ) Notice: Subject to any disclaimer, the term of this patent is extended or adjusted under 35 U.S.C. 154(b) by 1 day.

(21) Appl. No.: 14/859,192

(22) Filed: Sep. 18, 2015

(65) Prior Publication Data

US 2016/0007934 A1 Jan. 14, 2016

Related U.S. Application Data

(60) Provisional application No. 62/068,622, filed on Oct. 24, 2014, provisional application No. 62/067,914, (Continued)

(51) Int. Cl.
*A61B 5/11* (2006.01)
*A61B 5/00* (2006.01)
(Continued)

(52) U.S. Cl.
CPC .......... *A61B 5/1123* (2013.01); *A61B 5/0205* (2013.01); *A61B 5/02055* (2013.01); *A61B 5/1118* (2013.01); *A61B 5/4809* (2013.01); *A61B 5/4812* (2013.01); *A61B 5/681* (2013.01); *A61B 5/6801* (2013.01);
(Continued)

(58) Field of Classification Search
CPC .... A61B 2560/0209; A61B 2560/0219; A61B 5/11; A61B 5/1116; A61B 5/1118; A61B 5/1122; A61B 5/1123; A61B 5/4806; A61B 5/4809; A61B 5/4812; A61B 5/681; A61B 5/7246; A61B 5/7264; A61B 5/7282
See application file for complete search history.

(56) References Cited

U.S. PATENT DOCUMENTS 4,836,219 A 6/1989 Hobson et al.
5,724,990 A 3/1998 Ogino
(Continued)

FOREIGN PATENT DOCUMENTS

WO WO 2012/170586 12/2012
WO WO 2012/170924 12/2012
(Continued)

*Primary Examiner* — Adam J Eiseman
(74) *Attorney, Agent, or Firm* — Knobbe, Martens, Olson & Bear, LLP

(57) ABSTRACT

Aspects of generating movement measures that quantify motion data samples generated by a wearable electronic device are discussed herein. For example, in one aspect, an embodiment may obtain motion data samples generated by the set of motion sensors in a wearable electronic device. The wearable electronic device may then generate a first movement measure based on a quantification of the first set of motion data samples. The wearable electronic device may also generate a second movement measure based on a quantification of the second set of the motion data samples. The wearable electronic device may then cause the non-transitory machine readable storage medium to store the first movement measure and the second movement measure as time series data.

24 Claims, 19 Drawing Sheets

Related U.S. Application Data filed on Oct. 23, 2014, provisional application No. 62/063,941, filed on Oct. 14, 2014, provisional application No. 62/054,380, filed on Sep. 23, 2014.

(51) Int. Cl.
  *A61B 5/0205* (2006.01)
  *A61B 5/024* (2006.01)
  *A61B 5/053* (2006.01)
  *A61B 5/08* (2006.01)

(52) U.S. Cl.
  CPC .......... *A61B 5/7246* (2013.01); *A61B 5/7278* (2013.01); *A61B 5/743* (2013.01); *A61B 5/02405* (2013.01); *A61B 5/02416* (2013.01); *A61B 5/0533* (2013.01); *A61B 5/0816* (2013.01); *A61B 5/1121* (2013.01); *A61B 5/1122* (2013.01); *A61B 5/7264* (2013.01); *A61B 2560/0209* (2013.01); *A61B 2560/0242* (2013.01); *A61B 2562/0219* (2013.01); *A61B 2562/04* (2013.01)

(56) References Cited

U.S. PATENT DOCUMENTS

| | | | |
|---|---|---|---|
| 5,902,250 | A | 5/1999 | Verrier et al. |
| 6,964,641 | B2 | 11/2005 | Cho et al. |
| 7,306,567 | B2 | 12/2007 | Loree, IV |
| 7,578,793 | B2 | 8/2009 | Todros et al. |
| 7,674,230 | B2 | 3/2010 | Reisfeld |
| 8,002,553 | B2 | 8/2011 | Hatlestad et al. |
| 8,273,035 | B2 | 9/2012 | Russo et al. |
| 8,292,819 | B2 | 10/2012 | Kuo et al. |
| 8,548,770 | B2 | 10/2013 | Yuen et al. |
| 8,606,356 | B2 | 12/2013 | Lee et al. |
| 8,684,900 | B2 | 4/2014 | Tran |
| 8,690,751 | B2 | 4/2014 | Auphan |
| 8,712,723 | B1 | 4/2014 | Kahn et al. |
| 8,764,651 | B2 | 7/2014 | Tran |
| 8,793,522 | B2* | 7/2014 | Rahman ................ G06F 1/3296 713/320 |
| 8,812,259 | B2 | 8/2014 | Messenger et al. |
| 8,942,779 | B2 | 1/2015 | Halperin et al. |
| 2004/0087878 | A1 | 5/2004 | Krausman et al. |
| 2005/0043652 | A1 | 2/2005 | Lovett et al. |
| 2005/0209511 | A1 | 9/2005 | Heruth et al. |
| 2005/0209512 | A1 | 9/2005 | Heruth et al. |
| 2006/0020177 | A1 | 1/2006 | Seo et al. |
| 2006/0031102 | A1* | 2/2006 | Teller .................... A61B 5/411 705/3 |
| 2006/0224051 | A1* | 10/2006 | Teller ................ A61B 5/02055 600/300 |
| 2007/0161873 | A1 | 7/2007 | Ni et al. |
| 2007/0191742 | A1 | 8/2007 | Park |
| 2007/0208233 | A1 | 9/2007 | Kovacs |
| 2008/0287751 | A1 | 11/2008 | Stivoric et al. |
| 2009/0164219 | A1 | 6/2009 | Yeung et al. |
| 2010/0056907 | A1 | 3/2010 | Rappaport et al. |
| 2010/0102130 | A1 | 4/2010 | Madej et al. |
| 2010/0295684 | A1 | 11/2010 | Hsieh et al. |
| 2011/0252684 | A1 | 10/2011 | Ufer et al. |
| 2011/0295083 | A1 | 12/2011 | Doelling et al. |
| 2012/0142443 | A1 | 6/2012 | Savarese et al. |
| 2012/0316455 | A1 | 12/2012 | Rahman et al. |
| 2012/0316471 | A1 | 12/2012 | Rahman et al. |
| 2013/0018284 | A1* | 1/2013 | Kahn ................... G04G 13/026 600/595 |
| 2013/0096843 | A1* | 4/2013 | Yuen ................... A61B 5/0002 702/19 |
| 2014/0089243 | A1 | 3/2014 | Oppenheimer |
| 2014/0135594 | A1 | 5/2014 | Yuen et al. |
| 2014/0172362 | A1 | 6/2014 | Burton et al. |
| 2014/0176422 | A1 | 6/2014 | Brumback et al. |
| 2014/0176475 | A1 | 6/2014 | Myers et al. |
| 2014/0180022 | A1 | 6/2014 | Stivoric et al. |
| 2014/0200474 | A1 | 7/2014 | Selvaraj et al. |
| 2014/0316305 | A1 | 10/2014 | Venkatraman et al. |
| 2014/0316584 | A1 | 10/2014 | Matsuoka et al. |
| 2014/0364770 | A1* | 12/2014 | Slonneger ............ A61B 5/4812 600/595 |
| 2015/0026647 | A1 | 1/2015 | Park et al. |
| 2015/0057967 | A1 | 2/2015 | Albinali |

FOREIGN PATENT DOCUMENTS

| | | |
|---|---|---|
| WO | WO 2012/171032 | 12/2012 |
| WO | WO 2015/127067 | 8/2015 |
| WO | WO 2016/003269 | 1/2016 |

\* cited by examiner

MOVEMENT MEASURE GENERATION IN A WEARABLE ELECTRONIC DEVICE

CROSS-REFERENCE TO RELATED APPLICATIONS

This application claims the benefit of U.S. Provisional Application No. 62/054,380 filed Sep. 23, 2014, which is hereby incorporated by reference in its entirety; U.S. Provisional Application No. 62/063,941 filed Oct. 14, 2014, which is hereby incorporated by reference in its entirety; U.S. Provisional Application No. 62/067,914 filed Oct. 23, 2014, which is hereby incorporated by reference in its entirety; and U.S. Provisional Application No. 62/068,622 filed Oct. 24, 2014, which is hereby incorporated by reference in its entirety.

FIELD

The embodiments are related to the field of wearable electronic devices. Specifically, the embodiments are related to automatic movement detection utilizing a wearable electronic device.

BACKGROUND

Wearable electronic devices have gained popularity among consumers. A wearable electronic device may track user's activities using a variety of sensors and help the user to maintain a healthy life style. In order to determine a user's activities, a wearable electronic device collects activity data and runs computations on that data. One difficulty of obtaining accurate determinations of a user's activities is that these wearable electronic devices, because they are worn by a user, are typically packaged in a compact casing containing less powerful processor(s) (on which it is harder to run complex computations) than larger electronic devices.

Many wearable electronic devices may track metrics related to particular activities, such as a step count metric for running and walking activities. Other metrics that may be tracked by a wearable electronic device include metrics related to sleep. Typically, to initiate tracking of sleep metrics, a wearable electronic device may contain an interface for the user to provide notification that the user plans on transitioning into the asleep state (e.g., through the user pushing a button of or tap on the wearable electronic device).

BRIEF DESCRIPTION OF THE DRAWINGS

The embodiments described herein are illustrated by way of example, and not by way of limitation, in the figures of the accompanying drawings in which like references indicate similar elements.

DETAILED DESCRIPTION

Figure 1:
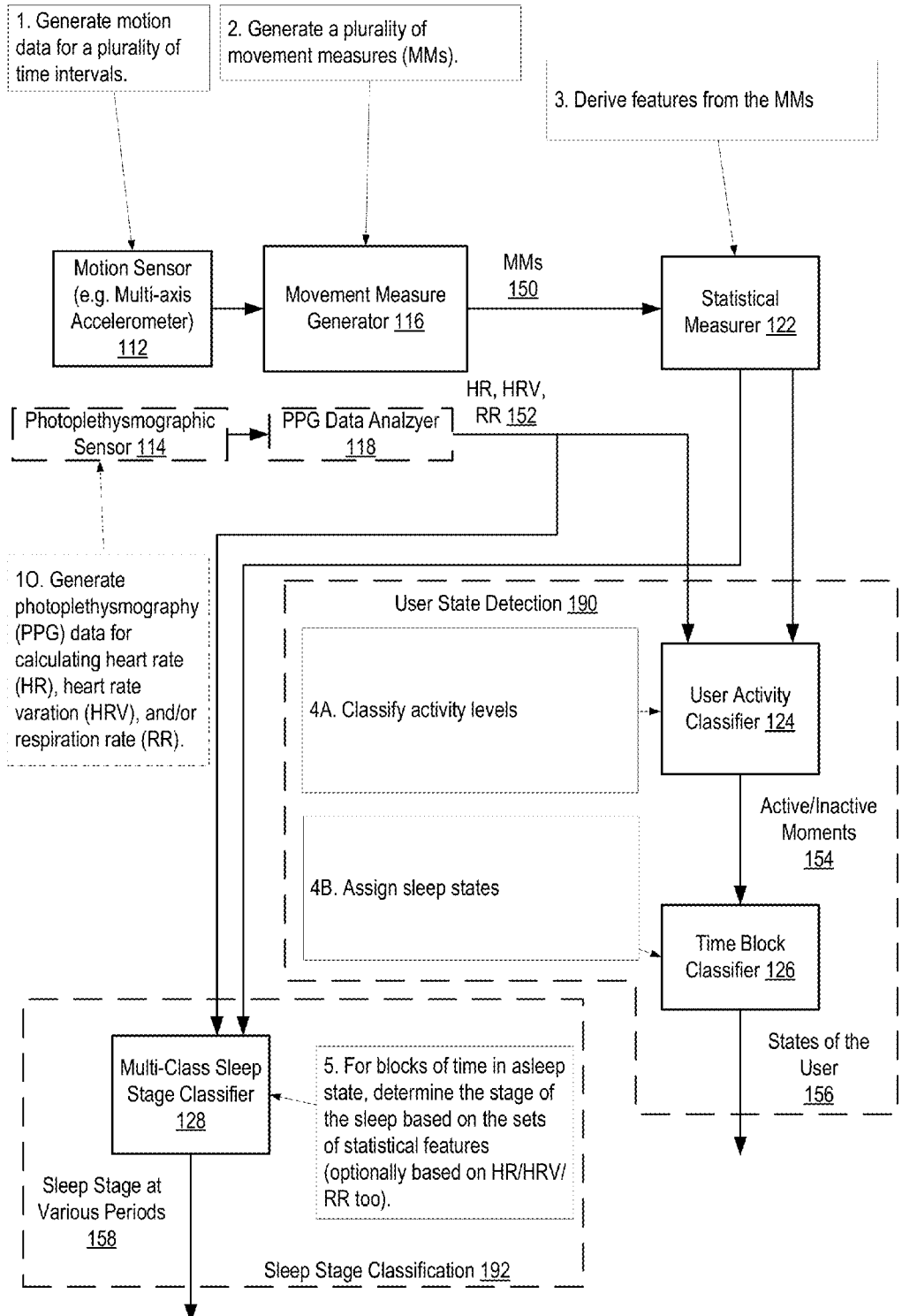
FIG. 1 illustrates user state detection and user sleep stage detection utilizing movement measures according to one embodiment of the invention.

Embodiments described herein may refer to operations and features of a wearable electronic device. A wearable electronic device may be configured to measure or otherwise detect motion experienced by the wearable electronic device. Such motion, for simplicity of discussion, may be described with reference to a display of the wearable electronic device, where the display is generally located on the user's forearm in the same place the display of a wrist watch would be located. While embodiments can be described with reference to a display of the wearable electronic device being generally located on the user's forearm in the same place the display of a wrist watch would be located, the scope of the invention is not so limited because modifications to a wearable electronic device can be made so that the wearable electronic device can be worn on a different location on the body (e.g., higher on the forearm, on the opposite side of the forearm, on a leg, on a torso, as eye glasses, and so forth) will be apparent to one of ordinary skill in the art.

Some example embodiments may involve a wearable electronic device that generates movement measures based on movement data generated by sensors of a wearable electronic device. A "movement measure," as used herein, may refer to data or logic that quantifies multiple samples of motion data generated by motion sensors of a wearable electronic device. In many cases, the movement measure will consume less memory to store than the aggregate of the multiple samples of motion data that the movement measure quantifies. In the case of accelerometer data, a movement measure may quantify acceleration data across multiple samples from the accelerometer along one or more axes. For example, a movement measure may be calculated every 30 seconds, where the movement measure quantifies the samples of accelerometer data generated for those 30 seconds. Further, the quantification can be a single number indicative of the degree of motion experienced across multiple axes for the multiple samples.

Although a movement measure can be used to decrease the memory consumed by storing multiple samples of movement data, it is to be appreciated that a movement measure is different than simply compressing the multiple samples of motion data. Such is the case because the compressed motion data generally would need to undergo decompression before being useful. That is, the compressed data itself, without decompression, generally does not represent a degree of movement for the time periods in which the motion data was sampled. In comparison, a value of a movement measure by itself can represent some notion of a degree of movement experienced during the timer intervals corresponding to the samples of motion data. In this way, one movement measure may be compared against another movement measure to determine a difference in the degree of motion experienced during different time intervals.

In an example embodiment, a wearable electronic device that is to be worn by a user may include a set of one or more motion sensors to generate motion data samples that represent motion of the wearable electronic device. The motion data samples include a first set of one or more motion data samples generated during a first time interval and a second set of one or more motion data samples generated during a second time interval. The wearable electronic device may be configured to (e.g., by a set of one or more processors executing instructions) obtain the motion data samples generated by the set of motion sensors. The wearable electronic device may then generate a first movement measure based on a quantification of the first set of motion data samples. The wearable electronic device may also generate a second movement measure based on a quantification of the second set of the motion data samples. The wearable electronic device may store the first movement measure and the second movement measure as time series data in a machine-readable storage medium.

Alternatively or additionally, some embodiments may automatically detect blocks of time where a wearer of the wearable electronic device is asleep. Here, automatic detection may refer to a detection that occurs without an explicit instruction from the wearer, such as traversing on-screen menus or otherwise inputting periods of time where the wearer is sleeping. It is to be appreciated that the term "automatic" does not preclude a case where the user may enable such a feature or act in a way that does not represent an explicit instruction of the timing when a user transitions between different sleep states. Such an embodiment that detects blocks of time in which the wearer is asleep may obtain a set of features for one or more periods of time from motion data obtained from a set of one or more motion sensors or data derived therefrom. Examples of data derived from the motion data may include the movement measures described above. An embodiment may then classify the one or more periods of time as one of a plurality of statuses of the user based on the set of features determined for the one or more periods of time. The statuses are indicative of relative degree of movement of the user. In some cases the statuses may be enumerated state values, such as active or inactive, where each state represent a different degree of movement. In other cases, the statuses may be numerical values or range of values that quantify the degree of movement. The embodiment may then derive blocks of time covering the one or more periods of time during which the user is in one of a plurality of states. The states include an awake state and an asleep state.

In some cases, some embodiments may operate to adjust the power consumption of a sensor based on the state of the user. For example, based on detecting that a state of the user, as tracked by a wearable electronic device, has transitioned into an asleep state, an embodiment may decrease power consumption of at least one sensor. Further, based on detecting that the state of the user, has transitioned out of the asleep state, an embodiment may reverse the decrease of power consumption of the at least one sensor.

In some cases, some embodiments may operate to detect when in time the wearable electronic device is not being worn by the user. Some embodiments that detect when the wearable electronic device is not being worn may automatically determine a period of time when the wearable electronic device is not being worn based on a comparison of motion data obtained from a set of motion sensors and a not-worn profile. The not-worn profile may be data or logic that specifies a pattern of motion data that is indicative of when the wearable electronic device is not worn by the user. The embodiment may then store, in non-transitory machine readable storage medium, data associating the period of time with a not-worn state.

Example embodiments are now discussed with reference to the Figures.

FIG. 1 illustrates user state detection and user sleep stage detection utilizing movement measures according to one embodiment of the invention. The task boxes and blocks of FIG. 1 may be implemented in a wearable electronic device, or distributed between the wearable electronic device and one or more other electronic devices coupled to the wearable electronic device. Electronic devices coupled to the wearable electronic device may be referred to herein as a secondary electronic device. A secondary electronic device may refer to a server (including hardware and software), a tablet, a smartphone (possibly executing an application (referred to as an app)), a desktop, or the like. A secondary electronic device can implement, for example, blocks 122/190/192. Additionally, or alternatively, a secondary device that provides sensor data can implement, for example, blocks 122 and/or 114. Task boxes 1-5 illustrate an example order in which operations may be performed by the components shown in FIG. 1. It is to be understood, however, that other embodiments may perform task boxes 1-5 in an order that differs from that shown in FIG. 1.

At task box 1, a motion sensor (e.g., a multi-axis accelerometer) 112 generates motion data samples that represent motion for a plurality of time intervals (e.g., the motion sensor 112 may be in a wearable electronic device and the motion data represent motion of that device). The motion sensor may generate a number of motion data samples during a time interval. The number of samples generated in a time interval may depend on the sampling rate of the motion sensor and the length of time of the interval. In the case that the motion sensor is an accelerometer, the motion data samples may characterize a measurement of acceleration along an axis of movement. In some cases, a motion data sample may be a data value that consumes a given amount of storage (e.g., 64-bits, 32-bits, 16-bits, and so on). The amount of storage consumed by a sample may depend on the implementation of the accelerometer used in the embodiment and the communication interface used to transfer the samples from the motion sensors to memory accessible by the microprocessor of the wearable electronic device.

At task box 2, the movement measure generator 116 generates a plurality of movement measures based on the motion data samples. A movement measure may be used to reduce the storage space needed to store data that characterizes movement of the wearable electronic device over time. For example, in one case, a movement measure can quantify of a number of motion data samples generated for a given time period (e.g., over a 30 second time period) with a single value. Further, according to some embodiments, an individual movement measure may consume less storage space than a single motion data sample. For example, a movement measure may consume 4-bits, 8-bits, 16-bits, 32-bits, or any other storage size.

As is discussed in greater detail herein, there are a number of techniques for generating movement measures. For example, in one embodiment, the movement measure generator 116 may process movement data samples at the moment that the sensor device generates the sample or, additionally or alternatively, may process a block of motion data samples (e.g., samples for one or more time intervals) at a predetermined frequency or based on a number of samples.

The generation of movement measures can be used to determine user asleep/awake state, thus the movement measures can also referred to as sleep coefficients for those embodiments that determine sleep states. There are at least two base versions of the sleep detection method. The first is a motion sensor (e.g., an accelerometer) solution, which uses data from a three-axis motion sensor. The second uses a combination of data coming from a motion sensor and an optical heart rate monitor (HRM) module including a photoplethysmographic sensor 114.

At task box 3, the statistical measurer 122 may analyze the movement measures to derive a time series of values for one or more statistical features that characterize a user's movement. In some cases, the feature value for a given movement measure may depend on the movement measures near (e.g., as may be measured by proximity in a time series) the given movement measure. For example, some embodiments of the statistical measurer 122 may utilize a rolling window of movement measures to generate a feature value for a given movement measure. To illustrate, assuming the set of movement measures is represented as MM={$mm_0$, $mm_1$, . . . , $mm_n$, $mm_{n+1}$, . . . $mm_z$}, then the statistical measurer 122 may derive the feature value of $mm_n$ from the movement measures $mm_{n-w-1}$ to $mm_{n+w-1}$, where the window size is 2*w. Examples of statistical features that the statistical measurer can derive include, among others: a quantile (e.g., quartile of acceleration data), an inter-quantile range, measures of dispersion (e.g., Gini coefficients), measures of entropy, information in the frequency domain (e.g., a quantification of an amount of periodic motion and amount of periodic motion in two or more frequency bands). Other examples of features are discussed below.

At optional task box 1O, optionally a photoplethysmographic sensor 114 may be utilized to generate photoplethysmography (PPG) data to calculate heart rate (HR), heart rate variability (HRV), and/or respiration rate (RR). A photoplethysmographic sensor typically includes a light source and a photodetector. A common light source is a light-emitting diode (LED).

At task box 4A, once the values for the set of feature have been derived, the user activity classifier 124 may classify or otherwise label the periods of time corresponding with the statistical features with an activity level, such as an active level or an inactive level. In some cases, the user activity classifier 124 classifies or otherwise labels each statistical feature in the set of feature values, while, in other cases, the user activity classifier 124 may classify or otherwise label a subset of features in the time series for the features, such as every other feature value, every five feature values, every ten feature values, and so on.

At task box 4B, the time block classifier 126 uses the activity levels to assign blocks of time a sleep state selected from one of a plurality of sleep states. The sleep states can include, among other things, an awake state and an asleep state. As described in greater detail below, some embodiments may include sleep states that represent different stages of sleep of a user. Further, some embodiments may include sleep states that represent different types of non-sleeping activities (e.g., a restless state). Each block of time can span one or more of the periods of time characterized by the activity levels. In some cases, the activity levels covered by the blocks of time may be homogeneous activity levels, while other cases may allow for heterogeneous activity levels.

Thus, FIG. 1 illustrates a system that can efficiently and/or automatically determine when a wearer of a wearable electronic device is sleeping. For example, rather than storing all of the motion data obtained from a motion sensor and deriving sleep states directly from the raw motion data, the system may instead transform the multiple motion data samples for a time interval into a single numerical value represented by the movement measure. Further, in some cases, an activity level for a time period of time may be determined from multiple features derived from the movement measures of multiple time intervals.

The operations and components of FIG. 1 are now described in greater detail.

Movement Measures

As just described above, embodiments may use a wearable electronic device containing a motion sensor to measure motion data (e.g., acceleration data measured by an accelerometer) that are indicative of motion that the wearable electronic device has undergone. Also described herein, a movement measure may quantify. In some embodiments, each movement measure is a single numeric number generated based on a combination (e.g., addition, average, and the like) of a quantification of a distribution of the motion data along one or more axes of the motion sensor. The single numeric number is a compact representation of the user's motion, and, as described in the foregoing, it can be used to detect user's state, user's sleep stage, an activity level, and other types of status for the user.

Using the movement measure, quantified at some interval or frequency (e.g., each 30 seconds), embodiments create informative statistical features that characterize a user's movements over longer periods of time (e.g., 10 minutes). In one embodiment, the movement measures quantify user movements and behavior across a short interval of time (e.g., 30 seconds). More specifically, this metric quantifies the distributions of acceleration data (a type of motion data) along axes and combines them into a single numeric number. Let $a\_x$, $a\_y$, $a\_z$ represent time series arrays of accelerometer data measured along three axes sampled at some sampling rate (e.g., 20 Hz) over some interval of time (e.g., 30 seconds).

One embodiment of the movement measure uses the maximum and minimum acceleration along an axis to quantify the distribution of acceleration along that axis. The separate values from each axis are summed together into a single metric for each 30 second interval (other intervals are possible as well). The movement measure generated from a set of motion data generated over a time period may then be expressed as:

$$MM = \max(a\_x) - \min(a\_x) + \max(a\_y) - \min(a\_y) + \max(a\_z) - \min(a\_z)$$

A more general form of this metric allows for different weighting along different axes and different exponential powers for each axis. $w\_x$, $w\_y$, $w\_z$ are weighting factors and $\exp\_x$, $\exp\_y$, $\exp\_z$ are exponents. The movement measure may be expressed as:

$$MM = w\_x * (\max(a\_x) - \min(a\_x))^{\wedge}\exp\_x +$$
$$w\_y * (\max(a\_y) - \min(a\_y))^{\wedge}\exp\_y +$$
$$w\_z * (\max(a\_z) - \min(a\_z))^{\wedge}\exp\_z$$

It is to be appreciated that some embodiments may perform a number of other post-processing operations on a movement measure. For example, in other embodiments, a movement measure generator may perform operations with saturation (the calculated movement measures are clamped to the boundary values supported by a number of bits used to store those calculated values). In some embodiments, a movement measure generator may cast the calculated movement measure into a 4 bit variable (or 8 bits, 16 bits), which may, in some cases, minimize data volume. In some embodiments, the frequency of occurrences of the calculated movement measures being saturated may be utilized to determine a threshold above which the casting is shifted to generate the movement measures (e.g., to account for "noisier" motion sensors which cause the meaningful data to be in higher order bits of the calculated movement measures). For example, in an embodiment that uses 4 bits to represent the movement measures, a shift of zero means the casting of the movement measures is from bit positions 3:0 of the calculated movement measures, a shift of 1 means the casting of the movement measures is from bit positions 4:1 of the calculated movement measures, and so on.

In one embodiment, a calculated movement measure comprises a combination of a statistical measure of the motion data along one or more axes. The statistical measure of the motion data may be one or more of a quantile (e.g., quartile of acceleration data), an inter-quantile range, measures of dispersion (e.g., Gini coefficients), and measures of entropy. In addition, the statistical measures can use information in the frequency domain in one embodiment. The information in the frequency domain may be used to quantify an amount of periodic motion and compare the amount of periodic motion in two or more frequency bands.

Other methods of quantifying the distributions of motion data, including accelerometer data, are also possible:
  Using the standard deviation rather than the maximum minus the minimum
  Using the interquartile range of motion data.
Other methods for quantifying user movements are also possible, such as:
  Using the temporal derivative (also known as jerk, surge, or lurch) of motion data along each of the three axes.
  Measuring deviations of total acceleration from 1 G (the gravitation acceleration at sea-level on Earth).
  Using integrals of the accelerometer data (e.g., first integral is velocity, second integral is position).

Note although acceleration data measured by an accelerometer is given as an example of motion data, other sensors (e.g., a gyroscope, a gravity sensor, a rotation vector sensor, or a magnetometer) may be used to collect other types of motion data to generate movement measures.

The advantage of utilizing movement measure is that it is very cheap to operate on an embedded device. For example, in some embodiments, single numeric values of movement measures may capture sufficiently meaningful information to perform the determinations described later herein, but require relatively little power to calculate, require relatively little storage space to store, require less bandwidth to transmit, etc. Further, a limited number of bits may be used to represent the movement measure (e.g., as described above, the movement measure can be cast to a 4 bit variable), which minimizes data volume. As discussed above, the movement measure may be transferred off the wearable electronic device to a computer server, or an application on an electronic device (an app on a mobile phone or tablet, for example) for further processing, such as making determinations of the state of the user.

Statistical Measures of User Movement

As previously described with reference to task box 3 shown in FIG. 1, the statistical measurer 122 may perform statistical measures to generate feature values for a given time. A user's non-instantaneous behavior can be characterized using distributions (and distribution-derived features) of movement measures over various timescales or window sizes (e.g., 5, 10, 40 minute intervals). One embodiment of the statistical measurer 122 uses rolling windows centered on the moments of interest (the time to which the feature value is assigned). For example, a feature value $F_N$ using a W minute window centered at time T will describe a characteristic of the distribution of movement measures extending from T−W/2 to T+W/2. In other embodiments, the statistical measurer 122 may use rolling windows that are left- or right-aligned to time T in order to consider only data that occurred previous to time T or after, respectively. The rate in which the feature values are calculated can correspond to the rate in which the movement measurements are generated, the window size, or any other suitable rate. For example, the next feature (e.g., $F_{N+1}$) may correspond to time T+W, T+W/X (where X is any numerical value), T+MMI (where MMI represents the interval of the movement measurement (e.g., 30 seconds according to some embodiments), or T+X.

For determinations of the user's state, multiple sets of statistical features over multiple sets of time windows may be utilized in one embodiment. Exemplary statistical features are:

The rolling fraction of movement measures values below a threshold value (e.g., 0.13 g or any other suitable value)

The rolling fraction of movement measures above a threshold value or between a range of thresholds (e.g., above 0.17 g or between 0.17 g and 0.20 g) or any other suitable value The rolling fraction of contiguous movement measures that are above a threshold value (e.g., 0.2 g) or any other suitable value Various rolling quantiles, averages, standard deviations, and other summary statistics of these distributions.

Information from Optical Photoplethysmography (PPG)

As illustrated in FIG. 1, at optional task box 1O, optionally a photoplethysmographic (PPG) sensor 114 may be utilized to generate PPG data to calculate heart rate (HR), HR variability (HRV), and/or respiration rate (RR). A PPG sensor typically includes a light source and a photodetector. A common light source is a light-emitting diode (LED).

PPG data can use used to calculate a user's heart rate by measuring the time between peaks or by calculating a dominant frequency in the optical signal. For most users, heart rate drops soon after onset of sleep and continues dropping over the course of sleep until early in the morning. Heart rate rises when the users wake up or during short disturbances during sleep. Measuring heart rate allows us to better identify periods of sleep. Further, heart rate is a good indicator to separate periods of sleep from periods of lying still, which could confuse a motion sensor like an accelerometer. Some users do not see this characteristic drop in heart rate with sleep. Such users can be identified after they wear the wearable electronic device for a few days and a different algorithm can be used on such users.

The difference of a user's heart rate from his/her average resting heart rate can be used as a personalized measure of how low his/her heart rate has dropped. The PPG data can also be used to calculate the respiration rate of the user. Respiration rate often shows distinct changes with sleep and can be used as a feature to identify periods of sleep. Respiration can be calculated using a number of techniques:

Measuring variabilities in the inter-peak intervals between heart beats

Measuring slow variabilities (0.1-0.5 Hz) in the baseline of the PPG signal

Measuring slow periodic signals (0.1-0.5 Hz) in the acceleration signal

In one embodiment, data representing the heart rate, heart rate variability, and/or respiration rate of the user of the wearable electronic device are calculated by the PPG data analyzer 118, and the resulting data (referred to as "analyzed PPG data") is an additional input to user activity classifier 124 and/or multi-class sleep stage classifier 128, in addition to the statistical features obtained through statistical measurer 122.

Classification Into Activity Levels

As previously discussed with reference to task box 4A shown in FIG. 1, the user activity classifier 124 may classify or otherwise label the statistical features associated with a time period with an activity level, such as being classified with an active level or an inactive level. In some embodiments, the user activity classifier 124 may include a classification model generated based on running a supervised machine learning algorithm on a set of sample features with known labels, such as a feature set associated with an active state (e.g., where the wearer is more likely to be awake) or an inactive state (e.g., where the wearer is more likely to be asleep).

In one embodiment, the user activity classifier is a decision tree, but a variety of other classifiers are possible, such as, by way of example and not limitation:

Random forests

Support vector machine

Neural network

K-nearest neighbor

Naïve Bayes

Hidden Markov Model

In addition, user activity classifier may use boosting to combine these various machine learning classifier models to make more accurate classification. The user activity classifier can, in one embodiment, post-process the classification models to remove noise and improve classification using binary-opening and binary-closing operations. A variety of other smoothing operations are possible, including median smoothing, weighted smoothing, Kriging, Markov models, etc.

The accuracy of the inferred transition points between user states can be improved using a variety of methods including edge-detection, changepoint analysis, etc.

As discussed above, the user activity classifier may use features derived from data other than motion data. Such non-motion data derived features that can also be incorporated into this classifier include:

Heart rate data, such as PPG

Skin or ambient temperature measurements or changes in temperature over time

Galvanic skin response

Ambient light measurement (e.g., people tend to sleep in dark environments)

Sound detection to detect patterns associated with sleeping, such as snoring, deep breathing, or relative little amounts of noise.

In one embodiment, the plurality of user activities include a third detected status denoting when a device is not being worn, and the "not-worn" status can be used to improve accuracy. This "not-worn" status can be inferred from the statistical features derived from the motion sensor, PPG data, and/or data from sensors such as temperature sensor, ambient light sensor, galvanic skin response sensor, capacitive sensor, humidity sensor and sound sensor.

For example, in the motion sensor only case, the "not-worn" state can be detected when the wearable electronic device remains in a particular orientation and/or is very still for too long, since this is uncharacteristic of human sleeping patterns. In the motion sensor+PPG sensor case, the "not-worn" state can be detected from the optical properties of the PPG data possibly in conjunction with a low-movement status (as measured using the motion sensor). Sleep onset and egress may also be inferred from the timing and duration of the "not-worn" state. Sleep estimates may improve for users over time in response to their editing of sleep onset and egress estimates (by using this feedback as training data or as priors when making classification predictions). While the "not-worn" state can be detected using motion sensor+PPG sensor, alternative embodiments that do not require a PPG sensor are discussed herein below.

Derivation of Awake and Asleep States

As discussed above with reference to task box 4B shown in FIG. 1, the time block classifier 126 derives from the activity levels over a set of periods of time, blocks of time which the user is in one of a plurality of sleep states. A sleep state can include an awake state and an asleep state. The blocks of time can span one or more of the periods of time assigned an activity level. Consecutive blocks of time can have different sleep states.

The time block classifier 126 can convert time periods assigned an active level or an inactive level into a sleep state based on empirically derived logic. Generally, active states imply a wake state and inactive states imply a sleep state, but a variety of contrary edge cases are accounted for during this conversion stage. For instance, a short inactive period (<60 mins) may be classified as "awake" time when there is appreciable step activity (>200 steps) immediately preceding and succeeding the inactive period (within 20 minutes). An example of where this may be helpful, is in correctly identifying hour long meetings where a user is sitting still as awake time and not a nap.

Through the automatic detection of a user's states, the user of the wearable electronic device no longer needs explicit user instruction that the user plans on transitioning into the asleep state, which can be inconvenient for a user of the wearable device and error prone, as users often forget to notify the wearable electronic device of the user's transition.

Sleep Stage Detection

Referring back to FIG. 1, the statistical features of motion measures can instead or also be used to classify a user's sleep stages (note the dashed boxes labeled user sleep state detection 190 and sleep stage classification 192). For instance, a wearable electronic device may implement user sleep state detection 190, but either not implement sleep stage classification or do such classification a different way. As another example, a wearable electronic device may implement sleep stage classification 192, but either implement user sleep state detection a different way or not at all (e.g., a wearable electronic device may contain an interface for the user to provide notification that the user plans on transitioning into the asleep state (e.g., through the user pushing a button of or tap on the wearable electronic device), and respond by enabling sleep stage classification 192 until the user wakes up (which transition back to the awake state may be determined through notification from the user or through automatic detection (as described herein or through a different technique)). Thus, the user sleep state detection 190 and the sleep stage classification 192 are independent, but may be use together. Referring back to FIG. 1, at task box 5, based on the sets of statistical features (optionally based on HR/HRV/RR too), multi-class sleep stage classifier 128 may determine the stages of the sleep of the user.

Human sleep patterns can be described in terms of discrete stages of sleep. At the highest descriptive level, these break down into REM (rapid eye movement), and non-REM sleep stages, the latter including various light and deep sleep stages. Patterns of movement, heart-rate, heart-rate variability (HRV), and respiration change according to sleep stage. These patterns can be detected using data from a motion sensor (such as a three axis accelerometer) along with a photoplethysmographic sensor that allows measurement of heart-rate, HRV, and respiration.

The data collected from the motion sensor and photoplethysmographic sensor includes:

Measures of user movement (see discussion of movement measures herein above)

Data for calculating heart-rate, heart rate variability, and respiration (e.g., as determined using data from the photoplethysmographic sensor in an electronic wearable device)

Time-domain or frequency-domain measure of heart-rate variability.

Statistical features may be derived using movement measures, and additionally, raw heart-rate data can be used to define a number of higher-level features. For example:

Rolling median or average heart rate on various timescales (e.g., over the last minute, last 5 minutes, etc.)

Rolling quantile of the heart rate distribution as measured on various timescales Whether heart rate exceeded/went-below some threshold over the course of some interval.

Additionally, statistical features may be derived using time derivative of heart-rate. For example:

Rolling maximum change in heart rate over various timescales

Rolling median, average, or some other quartile of the distribution of heart-rate derivative over various timescales Similar statistical features can be derived using heart-rate variability or respiration. For example:

Number of times HRV or respiration events exceeded some threshold over various timescales.

Rolling median, average, or some other quartile of the distribution of HRV or respiration over various timescales.

Heart rate, the derivative of heart rate, heart rate variability, and respiration may be normalized or standardized appropriately on a per user basis account for natural variation across users. For example, a user's resting heart rate may be subtracted from their instantaneous heart rate. Demographic information may also be used to renormalize features to account for variation according to demographics.

Then, the statistical features derived may be used to train a multi-class classifier (via supervised machine learning) 128 to classify periods of time as a particular sleep stage (e.g., REM, various stage of non-REM (NREM) such as light or deep sleep).

One embodiment uses a random forest classifier. Other classification methods include neural networks, hidden Markov models, support vector machines, k-mean clustering, and decision trees. Transitions between stages may also be detected using other change-detection methods, such as change point analysis, t-tests and Kolmogorov-smirnov statistics.

The resulting classification labels from the previous step can be smoothed to reduce noise. For example, the resulting classifications from a random forest classifier may be processed using an empirically calibrated Markov model that specifies the transitions probabilities between states. Other smoothing operations may include binary-erosion/dilation, median smoothing, etc.

Note that automatic user state detection and user sleep stage detection illustrated in FIG. 1 may be performed concurrently in a single system. The user state detection and user sleep stage detection may use the same or different statistical features to make their own determinations.

Illustrative Examples of User State Detection

Figure 2A:
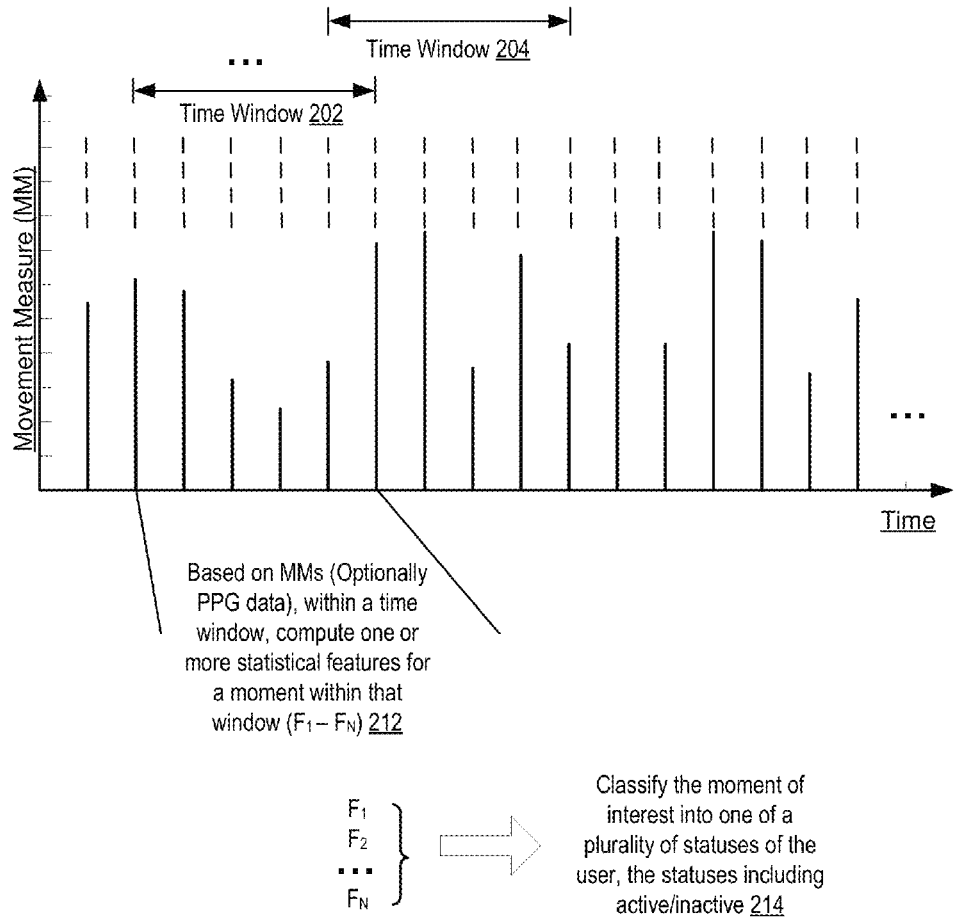
FIG. 2A illustrates movement measures collected at different time windows for moments of interest, as well as determining statistical features for one of the moments of interest and classifying that moment of interest based on the statistical features, according to one embodiment of the invention.

FIG. 2A illustrates movement measures collected at different time windows for moments of interest, as well as determining statistical features for one of the moments of interest and classifying that moment of interest based on the statistical features, according to one embodiment of the invention. As used herein, a "moment of interest" may refer to a given point in time, such as a period of time which may correspond to a movement measure, statistical feature, or state, and as such, a moment of interest may be used interchangeably with any suitable indication of a single point in time or a range of time periods. The movement measures are collected for each time interval (with reference to FIG. 1, reference 116 and task box 2). Based on the movement measures and optionally PPG data, within a time window, embodiments compute one or more statistical features for a moment within that window at reference 212 (with reference to FIG. 1, reference 122 and task box 3). A statistical feature may utilize movement measures from multiple time windows in one embodiment. The movement measure can have discrete values represented by a predefined number of bits. The statistical features $F_1$-$F_N$ determined for the moment of interest are used to classify the moment of interest into one of the plurality of activity levels of the user, the activity levels include active/inactive at reference 214 (with reference to FIG. 1, reference 124 and task box 4A).

Note while in one embodiment, the computation of one or more statistical feature uses movement measures at a consecutive subset of the time intervals that fall within a time window that includes the moment of interest, in an alternate embodiment, movement measures of other patterns (e.g., every other time interval) within the subset may be utilized for the computation.

Figure 2B:
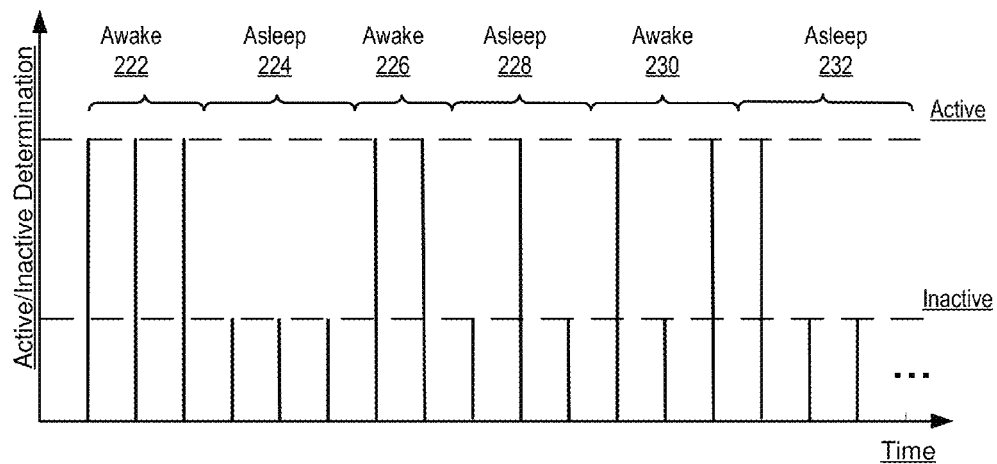
FIG. 2B illustrates classifying user active/inactive status and further deriving awake/asleep state based on the movement measure according to one embodiment of the invention.

FIG. 2B illustrates the use of the user's activity levels of active/inactive to derive awake/asleep stages according to one embodiment of the invention. As illustrated, the activity levels are illustrated as either active or inactive over time (at each moment of interest). From the active/inactive levels, embodiments derive non-overlapping, consecutive blocks of time during each of which the user is in one of a plurality of states; where the states include an awake state and an asleep state, where each of the blocks of time span one or more of the moments of interests, and where consecutive ones of the blocks of time have different ones of the plurality of states (with reference to FIG. 1, block 126 and task block 4B). Specifically, FIG. 2B illustrates the following blocks of time are derived: awake 222, asleep 224, awake 226, asleep 228, awake 230, and asleep 232; each of which spans multiple moments of interest. By way of example, a given block of time may include moments of time that were classified into different user states (e.g., asleep 228). The transitions in the user's states are represented by the edges of the blocks of time (i.e., when one block ends and the next begins—e.g., the user transitions from the awake state to the sleep state at the end of the block of time 222/beginning of block 224).

Figure 3A:
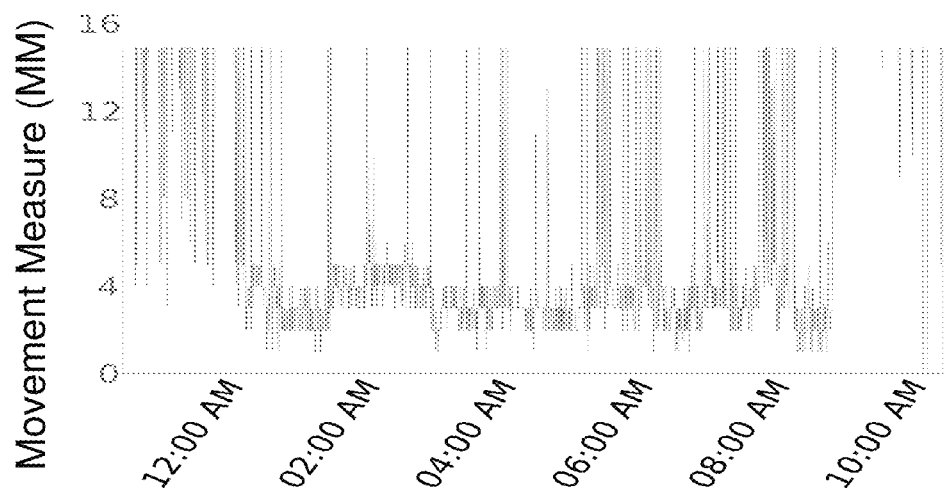
FIG. 3A illustrates movement measure snapshots taken from data during different time spans according to one embodiment of the invention.

FIG. 3A illustrates movement measure snapshots taken from data during different time spans according to one embodiment of the invention. The movement measures are represented by 4 bits, thus 16 different values starting from 0 to 15 (with offset of +1). Any values higher or lower than the 15 values are clamped to the highest (15) and lowest values (0). The time span is between 10:00 pm to 10:00 am, and the movement measures changes dynamically.

Figure 3B:
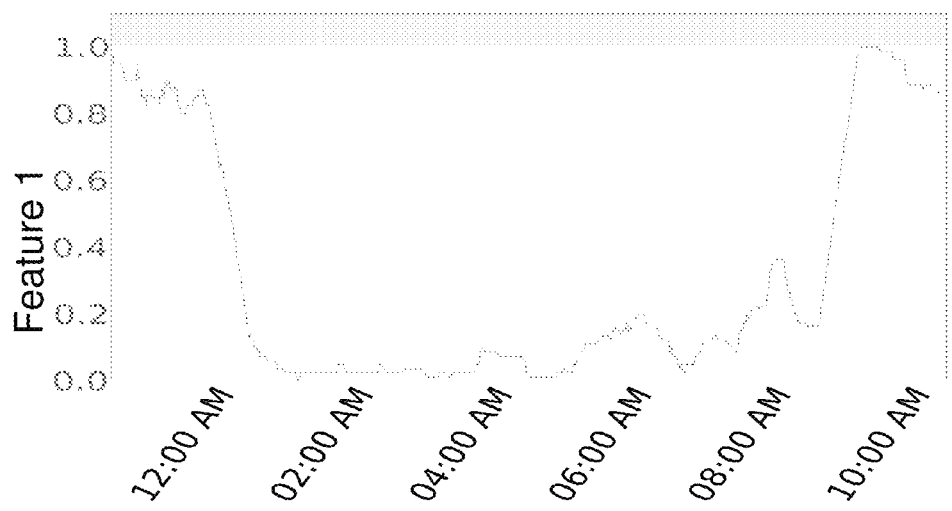
FIG. 3B illustrates the determination of a statistical feature for moments of interest using data during different time spans according to one embodiment of the invention.

FIG. 3B illustrates determination of a statistical feature for moments of interest using data during different time spans according to one embodiment of the invention. The feature (Feature 1) is calculated for every 30 second interval of time using a rolling window. Feature 1 uses movement measures between 20 minutes in the past and 20 minutes in the future. For example, the calculation of Feature 1 at 4:00 am may proceed as follows. The movement measures generated between 3:40 am and 4:20 am are stored in an array. If the movement measures are generated at 30 second intervals, there may be 40 minutes×2 values/minute+1 movement measures. The "+1" accounts for the moment of interest corresponding to 4:00 am. The statistical features that can be determined include the mean, standard deviation, $75^{th}$ quartile (or any other suitable quantile), etc. In this example, the statistical feature is to find the number of movement measures greater than a threshold value, such as 12. For each moment of interest, a percentage of a number of movement measures within the associated window greater than the threshold value (e.g., in the above example, 12) is recorded as the value of Feature 1 at the moment of interest. That is, $F_1$=(a number of movement measures with values>than the threshold value (e.g., 12))/total number of movement measures of the window.

Figure 3C:
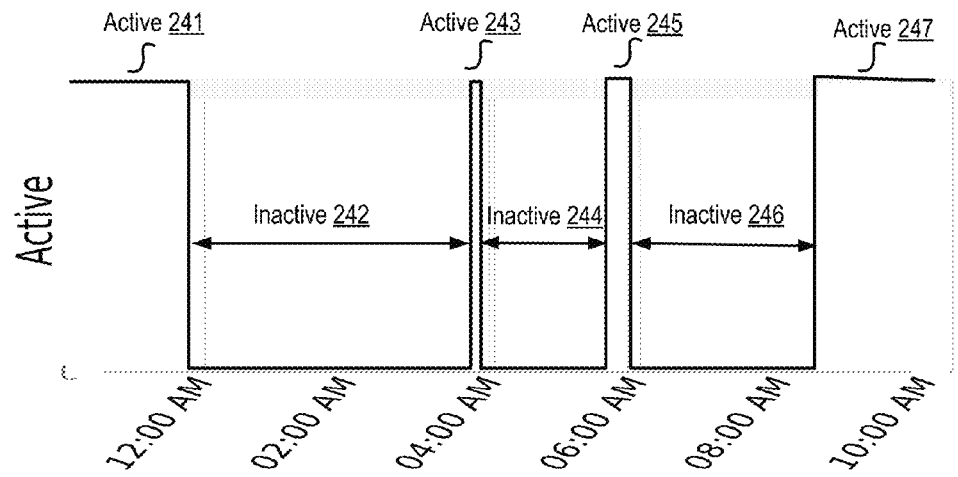
FIG. 3C illustrates the classifying user active/inactive status at moments of interest at the live system during different time spans according to one embodiment of the invention.

FIG. 3C illustrates the classifying user active/inactive activity levels at moments of interest using data during different time spans according to one embodiment of the invention. As illustrated, based on statistical features discussed herein above, it is determined that user is active until 12:00 am (reference 241). The status of the user turns to inactive between 12:00 am and 4:00 am (reference 242), after which the status of the user is active for a time period (reference 243), and goes back to inactive state (reference 244), and then returns active at reference 245. Afterward, the user toggles between inactive (reference 246) and active (reference 247). With respect to FIG. 3C, the time period of time covered by active period 241 may, for example, signify that the moments of interests (not shown) within the active period 241 were classified with active statuses.

Figure 3D:
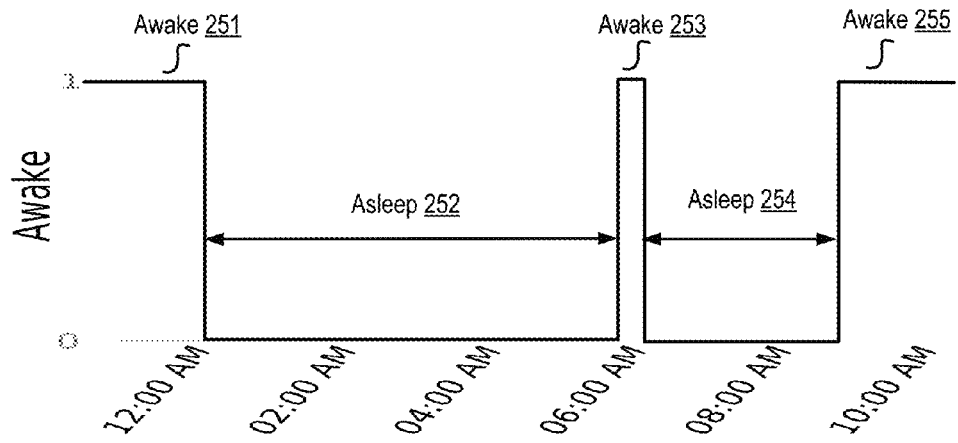
FIG. 3D illustrates the deriving user awake/asleep state using data during different time spans according to one embodiment of the invention.

FIG. 3D illustrates the deriving of user awake/asleep states using data during different time spans according to one embodiment of the invention. For most moments of interest, the active statuses result in deriving the user state being awake, and inactive statuses result in deriving the user state being asleep. However, from the inactive 242 (representing moments of interest(s) classified as inactive), active 243 (representing moments of interest(s) classified as active), and inactive 242 (representing moments of interest(s) classified as inactive), FIG. 3C illustrates that an asleep state is derived (reference 252). That is, the user may be classified as in the active status for some moments of interest, the user may still be determined to be in the asleep state. Embodiments may classify a time span with an "active" status as an asleep state if certain criteria are met. For example, if a user has a restless period where active and still moments are interspersed. Embodiments may employ a majority rules decision, using the statuses of the individual moments comprising the time-span, in the situation where the preceding time span was classified as an asleep state, the succeeding time span has an inactive status, and the current "active" time-span has a length within some specific range (10 -120 minutes).

Figure 3E:
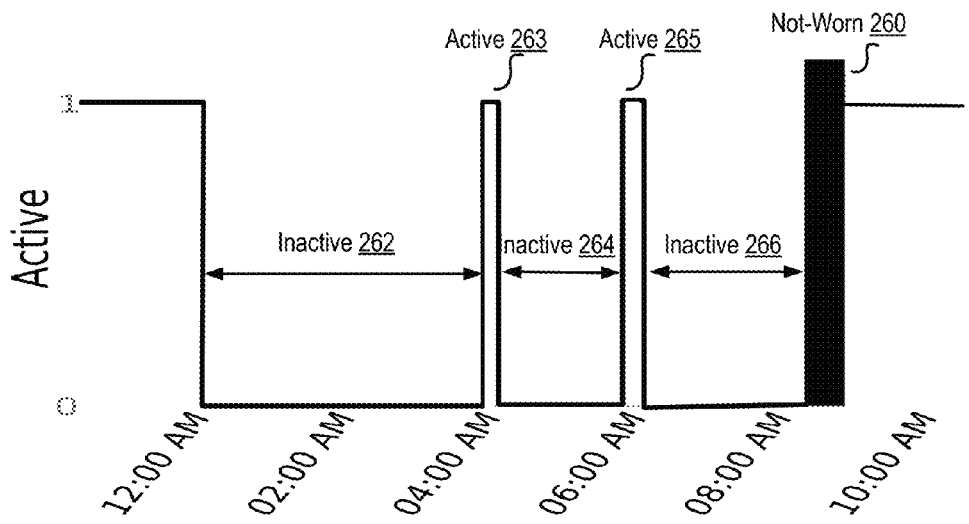
FIG. 3E illustrates the deriving user active/inactive/not-worn status at the live system during different time spans according to one embodiment of the invention where not-worn status is included.

FIG. 3E illustrates the deriving of user statuses (e.g., active/inactive/not-worn status) using data during different time spans according to one embodiment of the invention where not-worn status is included. The not-worn status is at reference 260 (representing moments of interest (not shown) classified as not-worn), where the embodiment determines that the user is not wearing the electronic wearable device around 9:00 am.

Figure 3F:
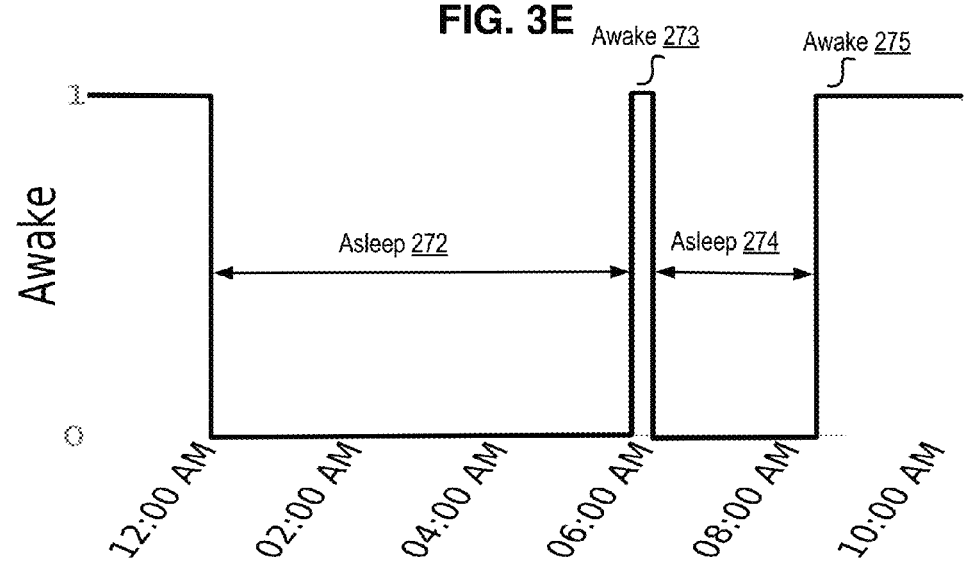
FIG. 3F illustrates the deriving of user's user awake/asleep state using data during different time spans according to one embodiment of the invention where not-worn status is considered.

FIG. 3F illustrates the deriving of user awake/asleep states using data during different time spans according to one embodiment where not-worn statuses are considered. In the embodiment illustrated, the not-worn status was derived to be part of the awake state 275 based on an empirically derived logic—around 9 am, it is likely the user is in the awake state.

A number of embodiments may have rules for assigning a block of time a sleep state depending on an off-wrist state. For example, consider the case where the user wakes up and immediately takes off their device to take a shower. The movement measure may remain low during this time, so this time span would be classified as inactive and ultimately as asleep time. But, because this span of time is classified as not-worn, and the preceding state is "asleep", and the succeeding is "awake," embodiments can correct the asleep state by classifying this block of time as awake time. Conversely, in the middle of a user's sleep, they somehow satisfy the not-worn criteria. In this case, the "not worn" time span is preceded and succeeded by "asleep" time. In this case, embodiments may classify the not-worn period as asleep time since it's unlikely that the user actually took off the device in the middle of a sleep period.

Illustrative Examples of User Sleep Stage Detection

Figure 4A:
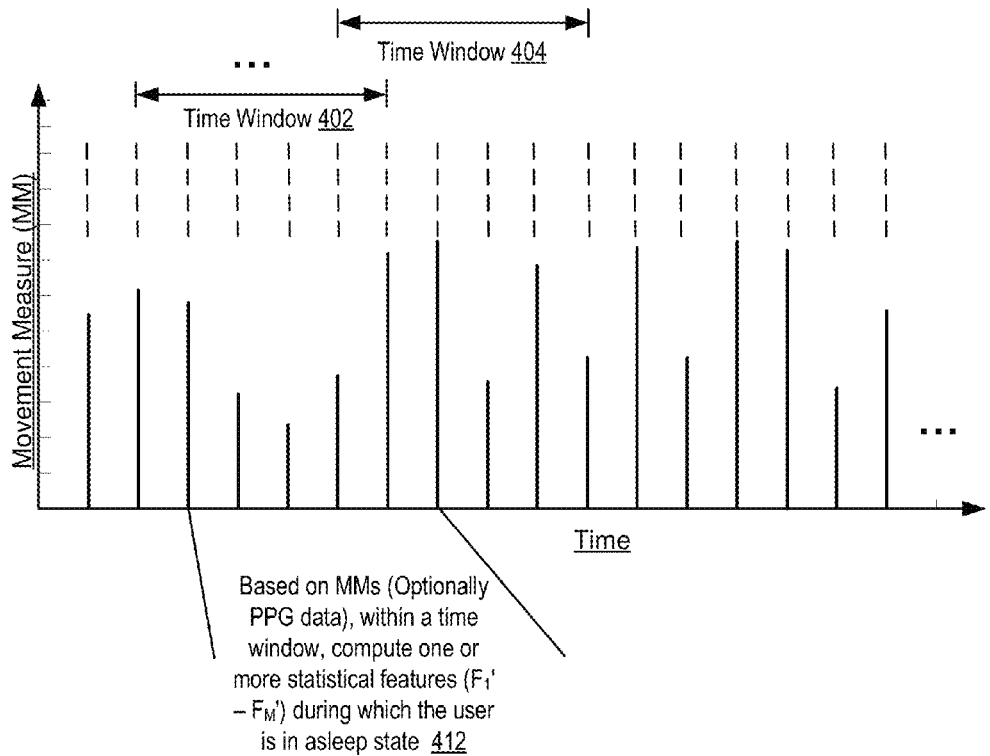
FIG. 4A illustrates the determining statistical features at different time windows for moments of interest, as well as determining statistical features for one of the moments of interest and classifying the moment of interest based on the statistical features according one embodiment of the invention.

FIG. 4A illustrates the determining of statistical features at different time windows for moments of interest, as well as determining statistical features for one of the moments of interest and classifying that moment of interest based on the statistical features, according one embodiment of the invention. FIG. 4A is similar to FIG. 3A, and the same or similar references indicate elements or components having the same or similar functionalities. The difference is that the statistical features may be different from what is utilized to determine user state. The statistical features $F'_1$ to $F'_M$ determined for the moment of interest are used to determine the sleep stage for the moments of interest.

Figure 4B:
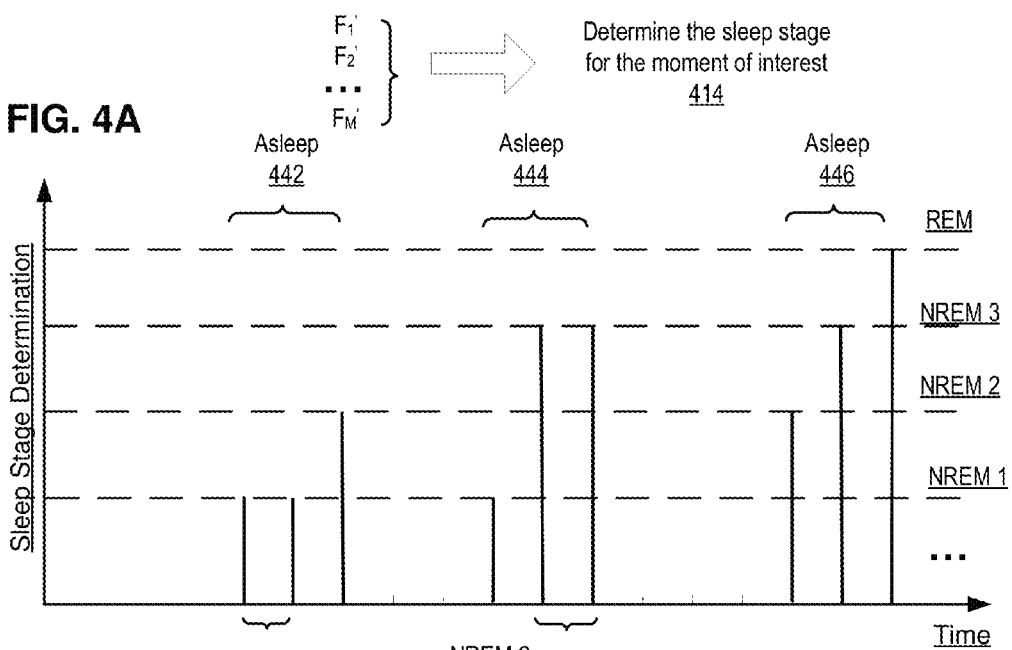
FIG. 4B illustrates the result of the determination of sleep stages for the moments of interest at different time windows according one embodiment of the invention.

FIG. 4B illustrates the result of the determination of sleep stages for the moments of interest at different time windows according one embodiment of the invention. In this embodiment, there are three NREM stages. Other embodiments may have different NREM stages.

Figure 5:
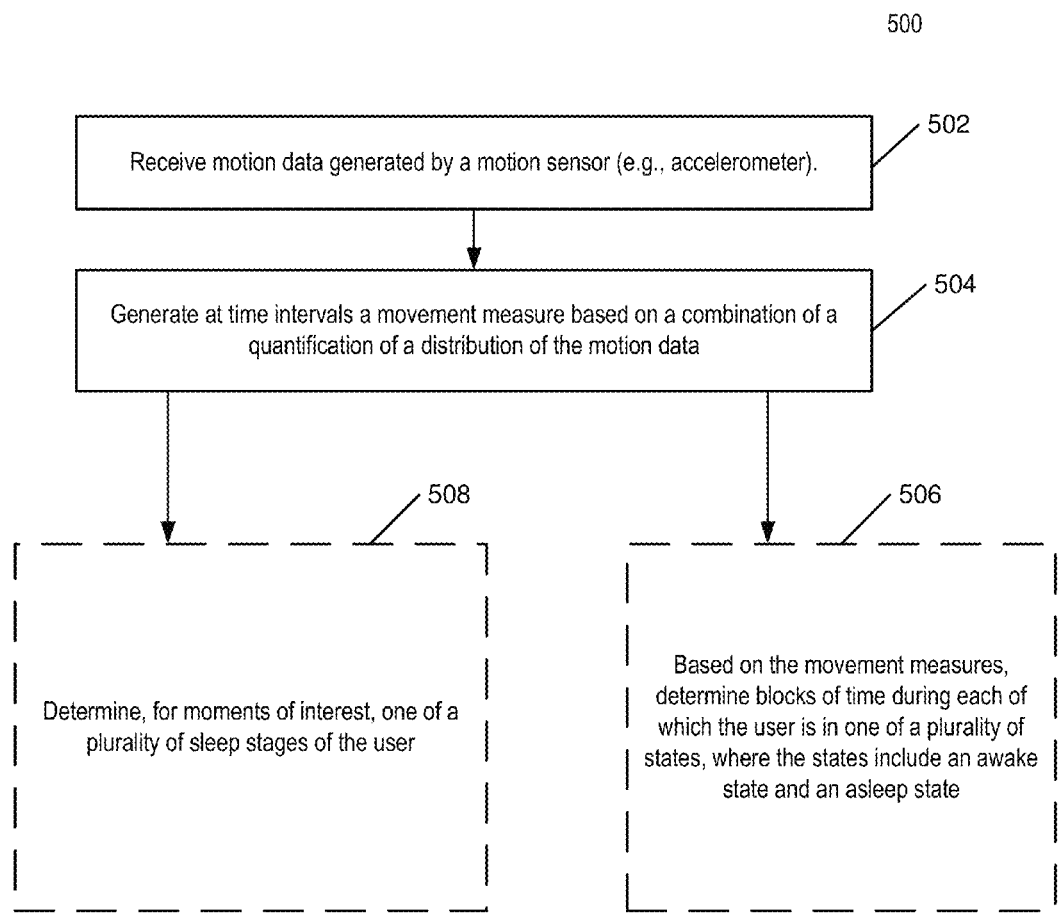
FIG. 5 is a flow diagram illustrating movement measure generation, and optional user state detection and/or user sleep stage detection, according to one embodiment of the invention.

Flow Diagram for Movement Measure Generation, User State Detection, and User Sleep Stage Detection FIG. 5 is a flow diagram illustrating movement measure generation, and optional user state detection and/or user sleep stage detection, according to one embodiment of the invention. The method 500 may be implemented in a wearable electronic device, an electronic device ((e.g., server (including hardware and software)/tablet/smartphone containing an application (referred to herein as an "app")) coupled to the wearable electronic device, or distributed between the two (e.g., references 502 and 504 may be implemented in a wearable electronic device, while references 506 and 508 may be implemented in an electronic device coupled to the wearable electronic device).

At reference 502, motion data generated by a motion sensor is received. The motion data may in some cases be accelerometer data received from an accelerometer (e.g., a three axis accelerometer) that represents motion along three axes. In an alternate embodiment, the motion sensor is a gyroscope, a gravity sensor, a rotation vector sensor, a location detection device (e.g., a GPS device, or a device capable of measuring movement using cell-phone or WiFi triangulation), or a magnetometer. While in one embodiment the motion sensor is in a wearable electronic device that may be worn on a user's body (e.g., arm, ankle, or chest) or embedded in user's garment, alternative embodiments may have the motion sensor data generated by another external electronic device and received by the wearable electronic device. The motion data may include multiple samples generated during different time intervals, such as a first time interval and a second time interval.

At reference 504, the wearable electronic device generates movement measures for time intervals (e.g., every 30 seconds) based on a combination of a quantification of the motion data generated during the respective time intervals. For example, in the case of acceleration data received from a three axes accelerometer, the wearable electronic device may quantify the acceleration data along each of the three axes during the first time interval and then quantify the acceleration data along each of the three axes during the second time interval. Thus, the multiple samples of acceleration data received from the two different time intervals are each quantified into a single numerical numbers. The different techniques that can be used to quantify multiple samples of motion data are described above.

Again, it is to be appreciated that a movement measure for a time interval may be a single numeric number. Further, the single numeric number can be represented by a predefined number of bits (e.g., four bits). In one embodiment, the number of bits is selected so that it is small enough for ease of transmission between different modules within the wearable electronic device or between the wearable electronic device and an electronic device coupled to the wearable electronic device, and large enough to represent sufficiently meaningful data for subsequent operations described herein.

Optionally at reference 506, based on the movement measures, sleep states may be assigned to blocks of time based on the movement measures. The states can include an awake state and an asleep state. The consecutive blocks of time may refer to different sleep states, such as a number of an asleep state for a first block of time and an awake state for a second block of time. As discussed herein, sleep states may be determined based on generating features for given points of time based on a window of movement measures. The features may then be used to assign activity levels to given points in time. The activity levels are then used to assign sleep states to the blocks of time.

Optionally at reference 508, for moments of interest, one of a plurality of sleep stages of the user is determined. Each of the moments of interest corresponds to one of the time intervals, and the determination for each of the moments of interest is based on the movement measures from a subset of the time intervals that fall within a time window that includes that moment of interest. The plurality of sleep stages include a rapid eye movement (REM) stage and a plurality of non-REM stages.

The movement measurements and/or the determined blocks of time with the states and/or the sleep stages may be presented to the user (e.g., on a display of the device or another electronic device (e.g., a tablet/smartphone/computer which receives the data from the wearable electronic device, generates the data, or receives the data from another electronic device (e.g., a server))) or stored in the wearable electronic device for a period in time sufficient to present or communicate such data to a secondary device.

Note that the quantification of the distribution of the motion data may be combined in a variety of ways as discussed herein above.

Flow Diagrams for Detecting User's Periods of Sleep and Sleep Stage

Figure 6:
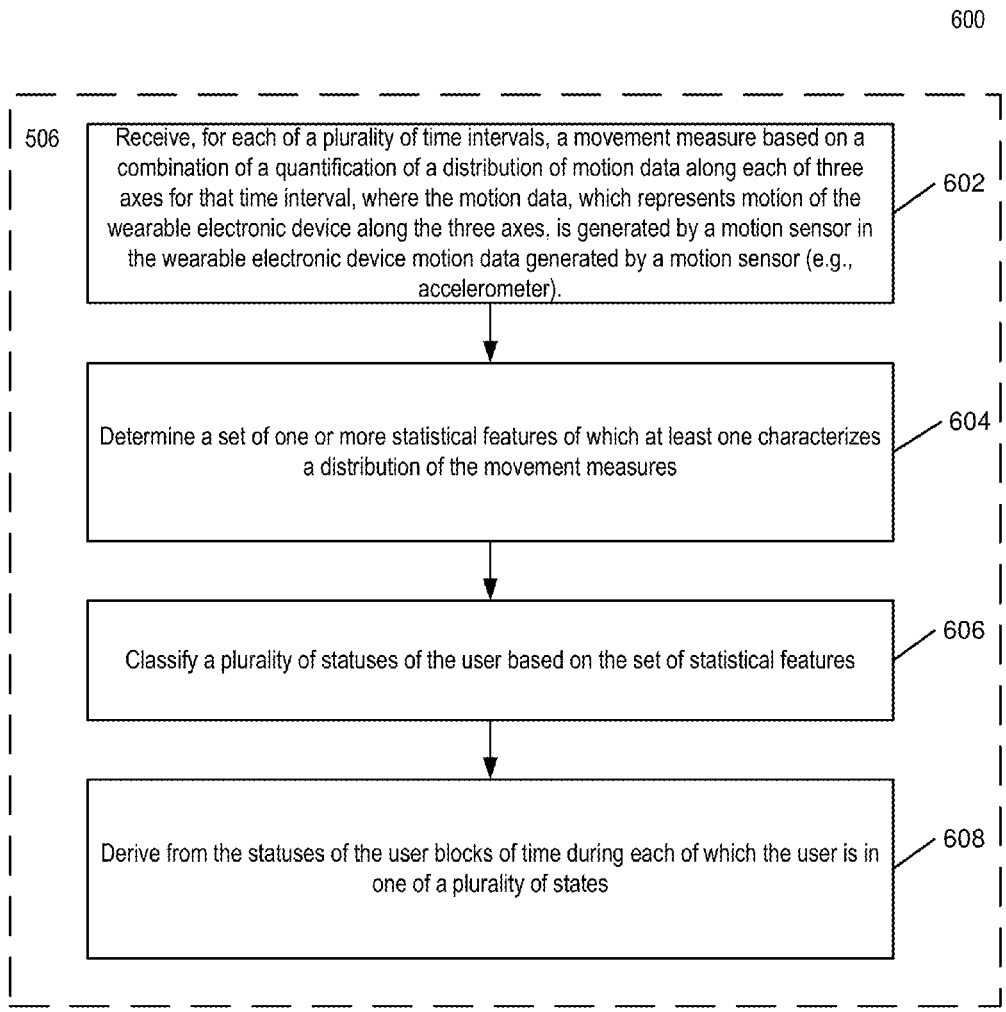
FIG. 6 is a flow diagram illustrating automatic detection of user's periods of sleep according to one embodiment of the invention.

FIG. 6 is a flow diagram illustrating a method 600 for automatic detection of user's periods of sleep according to one embodiment of the invention. Method 600 is an exemplary implementation of reference 506 of FIG. 5. The method 600 may be implemented in a wearable electronic device, an electronic device ((e.g., server (including hardware and software)/tablet/smartphone containing an application (referred to herein as an "app")) coupled to the wearable electronic device, or distributed between the two (e.g., references 602 and 604 may be implemented in a wearable electronic device, while references 606 and 608 may be implemented in an electronic device coupled to the wearable electronic device).

Reference 602 illustrates the receipt, for each of a plurality of time intervals, a movement measure based on a combination of a quantification of a distribution of motion data along each of three axes for that time interval. The motion data, which represents motion along the three axes, is generated by a motion sensor (which may be in a wearable electronic device, or provided to the wearable electronic device by another electronic device). The three axes can be orthogonal axes of the wearable electronic device in one embodiment. The motion measure may be generated by one or more the variety of motion sensors in a various ways such as discussed herein above relating to FIG. 1 and FIG. 5.

Reference 604 illustrates the determination, for each of a plurality of moments of interest, a set of one or more statistical features of which at least one characterizes a distribution of the movement measures determined for a subset of the time intervals that fall within a time window that includes the moment of interest. A moment of interest may refer to a specific time period of interest and may be used interchangeably with the phrase "a period of time." Each of the moments of interest corresponds to one of the time intervals, and the sets of statistical features characterize the user's movements. In some embodiments, the time window is a rolling window that centers, left-aligned, or right-aligned to the moment of interest. By way of example, the time window may be of various time scales such as 5, 10, 40 minute intervals while the time interval for movement measures is in smaller time scales such as 10, 30, 60 seconds. The subset of the time intervals selected are consecutive time intervals in one embodiment. In an alternate embodiment, the subset of the time intervals are selected in a different pattern such as every other time interval or every two time intervals. In one embodiment, one or more of the statistical features may be determined using multiple time windows at different time scales.

Reference 606 illustrates the classification of each of the plurality of moments of interest into one of a plurality of statuses (e.g., activity levels) of the user based on the set of statistical features determined for that moment, where the statuses of the user include active and inactive. In one embodiment, the classification is further based on PPG data generated by a PPG sensor (e.g., in the wearable electronic device or another electronic device which communicates the PPG data to the wearable electronic device). For example, the PPG data from a time window that includes the moment of interest is utilized to calculate at least one or more of the user's heart rate data, heart rate variability data, and/or respiration data (i.e., the analyzed PPG data). Reference 606 may be implemented in the various ways described above with regard to FIG. 1, reference 124 and task box 4A.

Reference 608 illustrates the derivation, from the statuses of the user at the moments of interest, non-overlapping, consecutive blocks of time during each of which the user is in one of a plurality of states. The states include an awake state and an asleep state, where each of the blocks of time spans one or more of the moments of interests, and consecutive ones of the blocks of time have different ones of the plurality of states. Reference 608 may be implemented in the various ways described above with regard to FIG. 1, reference 126 and task box 4B.

Figure 7:
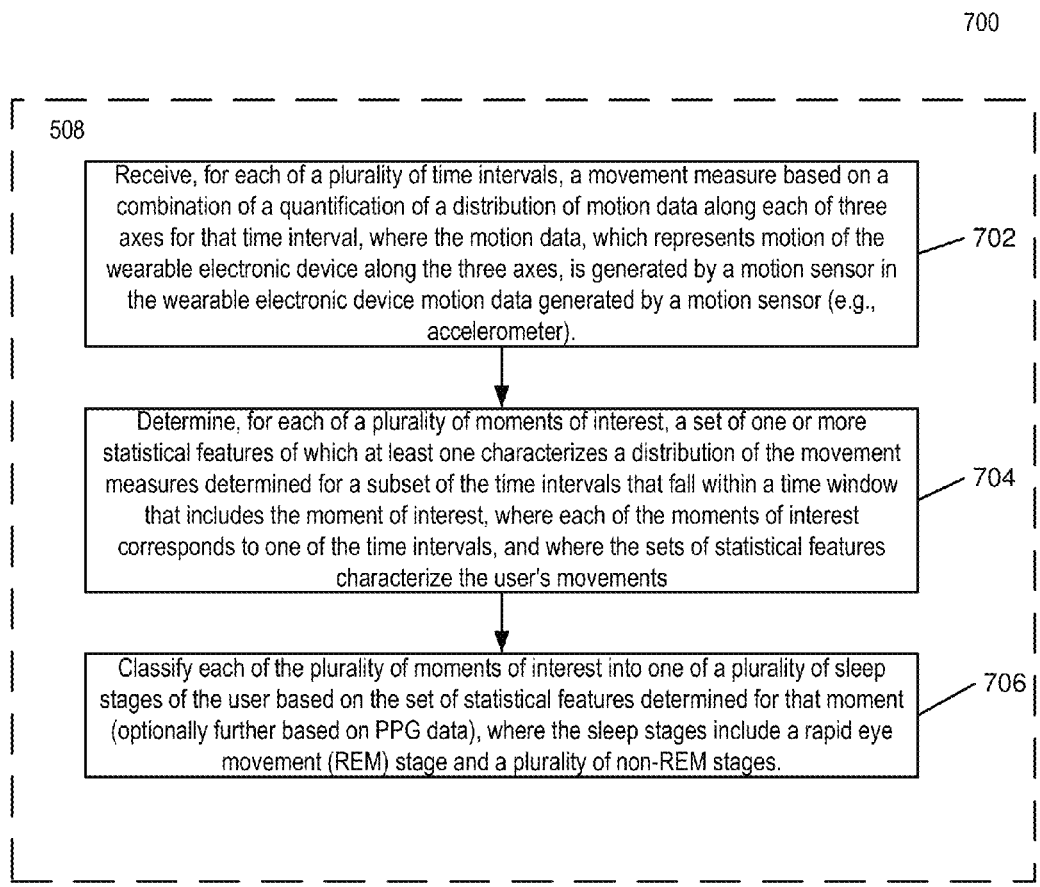
FIG. 7 is a flow diagram illustrating automatic detection of user's sleep stages according to one embodiment of the invention.

FIG. 7 is a flow diagram illustrating automatic detection of user's sleep stages according to one embodiment of the invention. Method 700 is an exemplary implementation of reference 508 of FIG. 5. Method 700 may be implemented in a wearable electronic device, an electronic device ((e.g., server (including hardware and software)/tablet/smartphone containing an application (referred to as an app) coupled to the wearable electronic device, or distributed between the two (e.g., references 702 and 704 may be implemented in a wearable electronic device, while reference 706 may be implemented in an electronic device coupled to the wearable electronic device).

Reference 702 illustrates the receipt of, for each of a plurality of time intervals, a movement measure based on a combination of a quantification of a distribution of motion data along each of three axes for that time interval. In an embodiment that implements both FIG. 6 and FIG. 7, references 602 and 702 may be the same.

Reference 704 illustrates the determination, for each of a plurality of moments of interest, a set of one or more statistical features of which at least one characterizes a distribution of the movement measures determined for a subset of the time intervals that fall within a time window that includes the moment of interest. Each of the moments of interest corresponds to one of the time intervals, and the sets of statistical features characterize the user's movements.

Reference 704 may be implemented in the various ways described above with regard to FIG. 1, references 122 and task box 3.

Reference 706 illustrates the classifying of each of the plurality of moments of interest into one of a plurality of sleep stages of the user based on the set of statistical features determined for that moment of interest. The sleep stages include a rapid eye movement (REM) stage and a plurality of non-REM stages. In one embodiment, the classification is further based on photoplethysmography (PPG) data generated by a photoplethysmographic sensor in the wearable electronic device. For example, the PPG data from a time window that includes the moment of interest is utilized to calculate at least one of the user's heart rate data, heart rate variability data, and respiration data. Reference 706 may be implemented in the various ways described above with regard to FIG. 1, references 128 and task box 5.

Note sleep stage detection of method 700 may be performed after it is determined that a user is in the asleep state, and the determination of the asleep state may be accomplished in different ways (e.g., through method 600, through a user interacting with an interface on a wearable electronic device (e.g., pushing a button or tapping the housing)).

Automatic Power Consumption Change of the Photoplethysmographic/Motion Sensor

In embodiments that can automatically detection a user's state and/or a user's sleep stage, the information may be used to change power consumption of various sensors such as a photoplethysmographic sensor and a motion sensor. For example, accurate measure of heart rate variability requires greater temporal precision in the signal compared to that required to measure heart rate, thus the light source of the photoplethysmographic sensor can be measured at a higher sampling rate and/or higher power for some fraction of the sleeping period (and/or an awake period) to achieve a better estimate of the heart rate variability. Similarly, accuracy of the measure of motion along the axes may be improved with a higher sampling rate, sensitivity, and/or power level, and this may be helpful for determining, for example, the user's sleep stage.

On the flip side, once it is detected that a user is in the sleep state, embodiments may reduce power consumption by the photoplethysmographic sensor and/or the motion sensor.

Figure 8A:
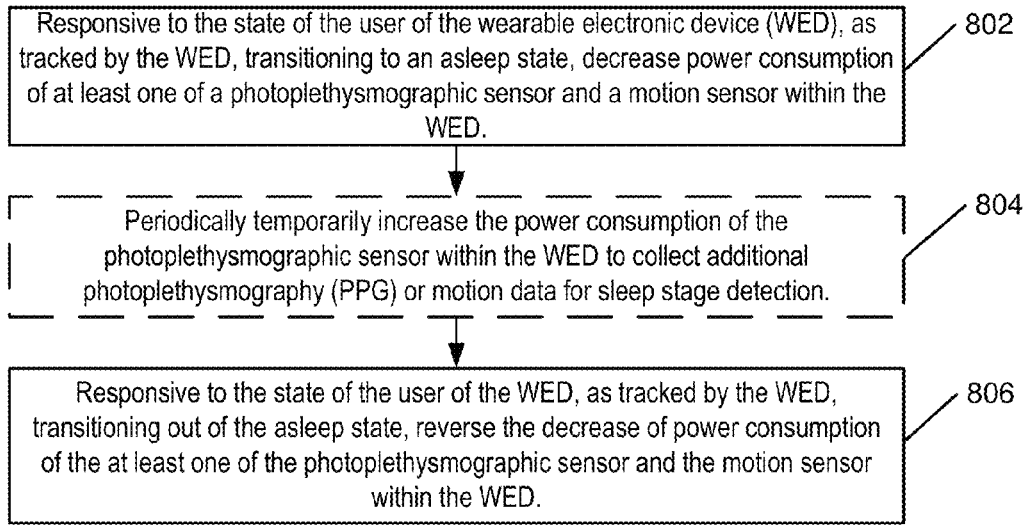
FIG. 8A is a flow diagram illustrating automatically reducing power consumption of at least one of a photoplethysmographic sensor and a motion sensor according to one embodiment of the invention.

FIG. 8A is a flow diagram illustrating automatically reducing power consumption of at least one of a photoplethysmographic sensor and a motion sensor according to one embodiment of the invention. The method may be implemented by a wearable electronic device that include a set of sensors including a motion sensor (e.g., an accelerometer) and a photoplethysmographic sensor, which contains a light source and a photodetector (e.g., a LED). At reference 802, responsive to a state of the user, as tracked by the wearable electronic device, transitioning into an asleep state, the wearable electronic device decreases power consumption of at least one of the photoplethysmographic sensor and motion sensor. Then optionally at reference 804, after the decrease, the wearable electronic device periodically temporarily increases the power consumption of the at least one of the photoplethysmographic sensor and motion sensor to generate additional data for sleep stage detection. At reference 806, responsive to the state of the user, as tracked by the wearable electronic device, transitioning out of the asleep state, the wearable electronic device reverses the decrease of power consumption of the at least one of the photoplethysmographic sensor and motion sensor.

In one embodiment, the decrease of the power consumption includes one of a decrease of a sampling rate of the photoplethysmographic sensor, a decrease of sensitivity of the photoplethysmographic sensor, a decrease of a power level of the light source of the photoplethysmographic sensor, an entry into a low precision state of the motion sensor, a decrease in sensitivity of the motion sensor, and a decrease of a sampling rate of the motion sensor. In one embodiment, the motion sensor is the accelerometer.

In one embodiment, the temporary increase of power consumption includes at least one of increase of a sampling rate of the photoplethysmographic sensor, increase of sensitivity of the photoplethysmographic sensor, increase of a power level of the light source, entry into a high precision state of the motion sensor, increase of sensitivity of the motion sensor, and an increase of a sampling rate of the motion sensor.

Figure 8B:
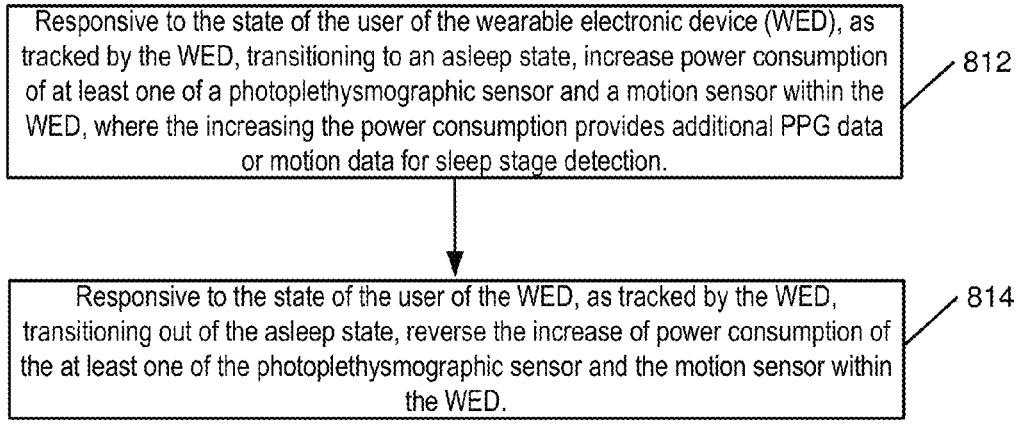
FIG. 8B is a flow diagram illustrating automatically increasing power consumption of at least one of a photoplethysmographic sensor and a motion sensor according to one embodiment of the invention.

FIG. 8B is a flow diagram illustrating automatically increasing power consumption of at least one of a photoplethysmographic sensor and a motion sensor according to one embodiment of the invention.

At reference 812, responsive to a state of the user, as tracked by the wearable electronic device, transitioning into an asleep state, the wearable electronic device increases power consumption of at least one of the photoplethysmographic sensor and motion sensor. As previously described, the increasing of the power consumption provides additional PPG data or motion data for sleep stage detection.

At reference 814, responsive to the state of the user, as tracked by the wearable electronic device, transitioning out of the asleep state, the wearable electronic device reverses the increase of power consumption of the at least one of the photoplethysmographic sensor and motion sensor.

While in one embodiment the tracking of the state of the user by the wearable electronic device for the methods of FIG. 8A or 8B is performed by the wearable electronic device, in an alternative embodiments the tracking of the state of the user is done with the assistance of one or more other electronic devices (e.g., server (including hardware and software)/tablet/smartphone containing an application (referred to as an app) which communicates back to the wearable electronic device in real time or near real time the user's state; as well as optionally sensors outside of the wearable electronic device (e.g., on the chest of the user, the mattress or bedside table of the user) that provide data to the server/table/smartphone to assist in detecting transitions in and out of the asleep state). Both of these approaches detect the user's state and are considered within the meaning of "as tracked by the wearable electronic device".

While in one embodiment the power consumption is changed responsive to the detection of a user's transitions in and out of the asleep state, alternative embodiments instead or in addition make sure power consumption changes responsive to detection of transition between one or more of the sleep stages.

The change of power consumption of the sensors may cause a visible change to the wearable electronic device. For example, the decrease of power consumption of the photoplethysmographic sensor may cause the light source to emit less light (decrease its illumination level) when the power level of the light source is reduced. Similarly, the increase of power consumption of the photoplethysmographic sensor may cause the light source to emit more light (increase its illumination level) when the power level of the light source is increased. Thus, the wearable electronic device may change its illumination level upon transitioning into and out of asleep state.

Figure 9:
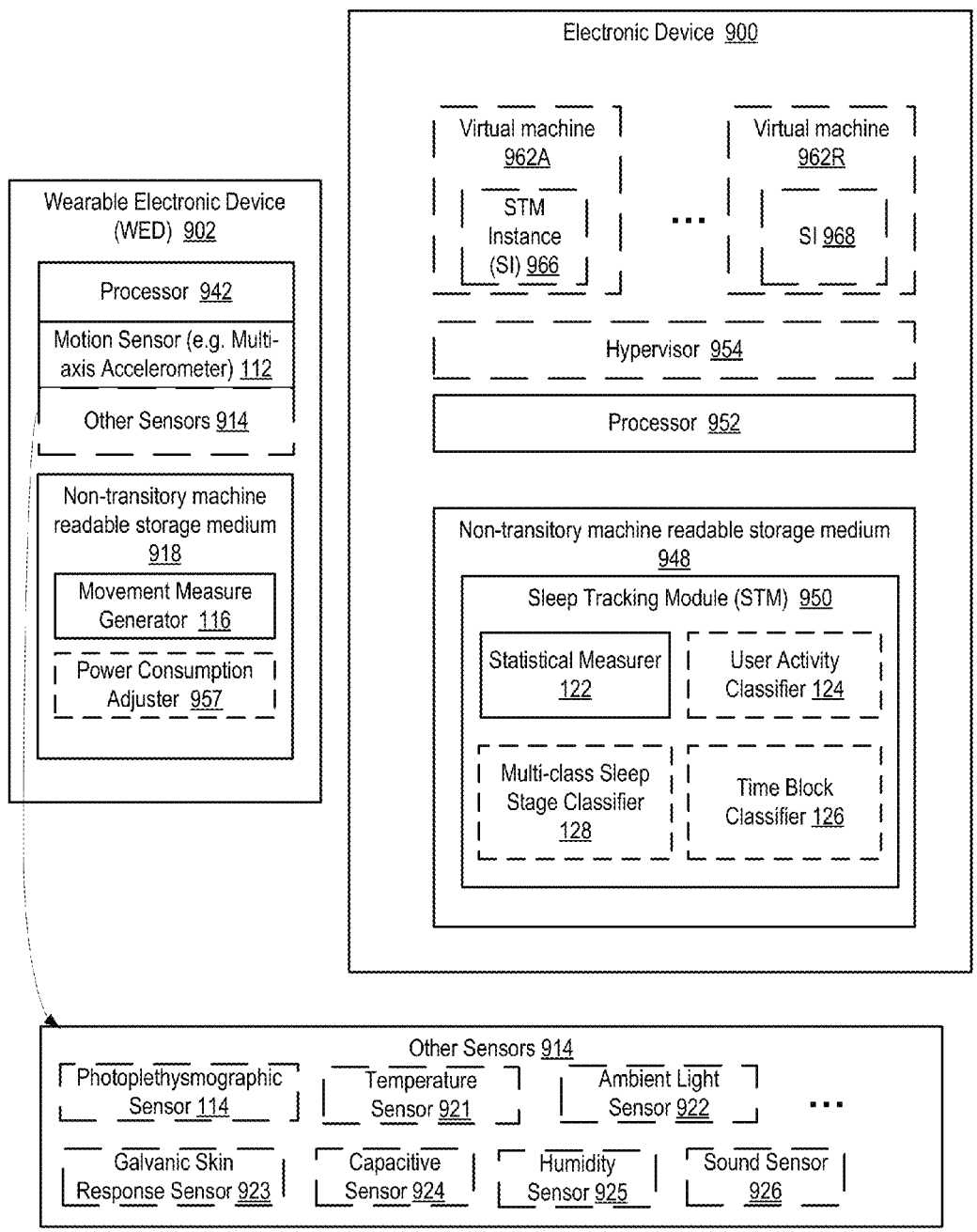
FIG. 9 is a block diagrams illustrating a wearable electronic device and an electronic device implementing operations disclosed according to one embodiment of the invention.

Exemplary Devices Implementing Embodiments with Movement Measures, Automatic Detection of User's Sleep Period/Stage, and Automatic Power Consumption Change As previously described, while in some embodiments the operations are implemented in a wearable electronic device, alternative embodiments distribute different ones of the operations to different electronic devices (FIG. 9 illustrates examples of one such distribution). FIG. 9 is a block diagrams illustrating the wearable electronic device and an electronic device implementing operations disclosed according to one embodiment of the invention. Wearable electronic device (WED) 902 includes processor 942, which may be a set of processors. WED 902 includes motion sensor 112, which may be a multi-axis accelerometer, a gyroscope, a gravity sensor, a rotation vector sensor, or a magnetometer as discussed herein above. WED 902 may also include other sensors 914, which may include photoplethysmographic sensor 114 illustrated in FIG. 1, temperature sensor 921, ambient light sensor 922, galvanic skin response sensor 923, capacitive sensor 924, humidity sensor 925, and sound sensor 926. WED 902 also contains non-transitory machine readable storage medium 918, which includes instructions that implement the movement measure generator 116 discussed above. When executed by processor 942, the movement measure generator causes wearable electronic device 902 to generate movement measures. In one embodiment, non-transitory machine readable storage medium 918 contains power consumption adjuster 917, which performs power consumption adjustment on at least one of motion sensor 112 and the PPG sensor 114 as discussed herein above.

In one embodiment, other sensors 914 are not within wearable electronic device 902. These sensors may be distributed around the user. For example, these sensors may be placed on the chest of the user, the mattress or bedside table of the user, while the wearable electronic device is worn by the user.

FIG. 9 also includes an electronic device 900 (e.g., server (including hardware and software)/tablet/smartphone executing an application (referred to as an app). The electronic device 900 may perform the functionalities relating to statistical measurer 122, user activity classifier 124, time block classifier 126, and/or multi-class sleep stage classifier 128, some or all of which are included in the sleep tracking module (STM) 950, which is stored in the non-transitory machine readable storage medium 948. When executed by processor 952, STM 950 causes electronic device 900 to perform the corresponding operations discussed herein above. Electronic device 900 may contain virtual machines (VMs) 962A to 962R, each of which may execute a software instance of STM 950. Hypervisor 954 may present a virtual operating platform for the virtual machines 962A to 962R.

Extensions and Enabled Applications

A variety of applications and extensions are possible around sleep using a variety of sensors.

Data from Wearable Electronic Device when Placed on or Near the Bed

A wearable electronic device can be used to monitor onset/egress of sleep as well as sleep stages even when not physically worn by the user. For example, an electronic device placed on the bed, on the pillow, in the pillow or on the bedside table can be used to measure a user's sleep. Such a device would use the accelerometer, microphone, ambient light sensor or video camera to measure a user's movement, heart rate or respiration. Such a video camera might have the functionality to illuminate the room and capture video in low light environments or infrared. These features can then be used to infer details of a user's sleep and sleep stage as described herein.

Similarly, a wall mounted device like an alarm clock could be equipped with a video camera and microphone which would measure a user's heart rate, respiration rate and movement and be used to infer details about sleep. Since a user is asleep, the user would be very stationary and this provides a good opportunity to estimate heart rate from video. Such a video camera might have the functionality to illuminate the room and capture video in low light environments or infrared. Also, such a camera could capture heart rate, respiration rate and movement of multiple users simultaneously. Thus, the movement measures and PPG data may be generated by sensors and data collection device outside of a wearable electronic device, and these movement measures and PPG data may instead and/or in addition to be provided through the wearable electronic device or through a more direct transmission (e.g., having their own WiFi connection, Bluetooth connection, or cellular connection) to an electronic device to infer details of a user's sleep and sleep stage as described herein.

Since a user is stationary during sleep, this provides an opportunity for such a system to measure more advanced metrics about the user like small changes in respiration rate or small changes in inter beat interval (of the heart). This information can be used to help detect or diagnose conditions like sleep apnea and atrial fibrillation.

Sleep Apnea Detection

Sleep apnea can be described as the disruption of normal breathing during sleep. Given the auto-detection of sleep, sleep apnea can be detected in multiple ways using a variety of combinations of sensors. For example:
  Reduction in blood oxygenation using pulse oximetry (e.g., as part of a PPG system utilizing PPG data);
  Disruption of normal audible breathing patterns as measured by an audio sensor
  Change in respiration rate as measured using the PPG system.
  Change in respiration using a strain gauge (e.g., worn around the chest)
  Change in respiration using an accelerometer (that measures the periodic accelerations of respiration)
  Change in respiration using a video camera that directly or indirectly observes respiration
  Change in respiration using a CO2 sensor that detects changes in expelled Carbon Dioxide.

Multi-User Sleep Tracking

The sleep patterns (e.g., sleep onset/egress, wakefulness, sleep stages) may be tracked for multiple users at a time. For example:
  An image recording device located on a bedside table could directly detect sleep by observing one or more users' state of motion, whether they are breathing in a way consistent with sleeping, by measuring their heart-rate and heart-rate variability by detecting the change in color of their skin with each heartbeat, etc.
  An image recording device could also directly detect the appearance or lack of rapid eye movement in one or more sleeping users, thus directly detecting the difference between REM and non-REM sleep stages.
  A smart mattress with one or more accelerometers could detect and separate motions from multiple sleeping users.
  An audio sensor could detect and disambiguate the respiration or snoring patterns for multiple users at a time.

Detecting the Cause of Sleep Disruptions

Some sleep disruptions may result as a consequence of physiological (e.g., sleep apnea) and/or environmental effects. These can be detected and correlated with sleep disruptions, which in turn could be used by a user to identify things or events that degrade his/her sleep. For example:

A temperature sensor (worn on the body, made as part of the bed, as part of a device sitting on a bedside table, etc.) could detect changes in temperatures that may lead to sleep disruptions.

An audio sensor could detect sounds that may disrupt or degrade a user's sleep.

An ambient light sensor could detect bright, persistent, intermittent, etc. lights that may disrupt sleep.

A humidity sensor could detect changes in humidity that may lead to discomfort or degraded/disrupted sleep.

An accelerometer could be used to detect motions (e.g., a large truck driving by, an earthquake, etc.) that may disrupt sleep.

Automatic Detection of when a Wearable Electronic Device is not being Worn Based on a Motion Sensor Some embodiments discussed herein may relate to a wearable electronic device capable of detecting when the wearable electronic device is not being worn. For example, depending on the arrangement between the housing and possibly a wristband, a wearable electronic device can detect when the wearable electronic device has been placed in one of a number of orientations that the wearable electronic device is commonly placed when not being worn. In some cases, these orientations may be specified by not-worn profiles. A "not-worn profile," as used herein, may be data or logic that specifies a pattern of motion data that indicates when a wearable electronic device is not worn by the user. In a given embodiment, the pattern of motion data (e.g., accelerometer data) may reflect the force of gravity detected by an inertia sensor (e.g., an accelerometer) along one or more axes.

While embodiments are described which reference to a three axis accelerometer oriented in the wearable electronic device a particular way, alternative embodiments may have a different orientation, which may require predictable changes in the techniques described herein, such as transforming the motion data from one coordinate system to another. To simplify the discussion of example embodiments, the negative direction of an axis is referred to the inverse of the axis.

By way of example and not limitation, a particular orientation for axes of motion detected by an accelerometer is now described relative to a display. Referring to the display of the wearable electronic device, worn on the user's forearm in the same place the display of a wrist watch would be worn, relative to a clock face: the X axis is along the line formed between 12 and 6 o'clock (the positive direction being the 12 to 6 direction) and may also be referred to as the top-bottom axis; the Y axis is along a line formed between 9 and 3 o'clock (that is, from the user's elbow to wrist if worn on the left hand) (the positive direction, in some cases, being the 9 to 3 direction) and may also be referred to as the left-right axis; the Z axis is along a line perpendicular to the clock face (the positive direction being out the front of the clock face) and may also be referred to as the back-front axis. Thus, in this example, the X-Y axes form a plane that contains the display/clock face and the X-Z axes form a plane that is perpendicular to the user's forearm.

In one embodiment of the wearable electronic device that is to be worn on the user's forearm has a housing that contains the electronics associated with the wearable electronic device, one or more buttons for the user to interact with, and one or more displays accessible/visible through the housing. The wearable electronic device also can include a wristband to secure the wearable electronic device to the user's forearm, according to one embodiment of the invention. As used herein, the term "wristband" may refer to a band that is designed to fully or partially encircle a person's forearm near the wrist joint. The band may be continuous, e.g., without any breaks (it may stretch to fit over a person's hand or have an expanding portion similar to a dress watchband), or may be discontinuous, e.g. having a clasp or other connection allowing the band to be closed similar to a watchband or may be simply open, e.g., having a C-shape that clasps the wearer's wrist.

Some example orientations are now described in greater detail.

Figure 10A:
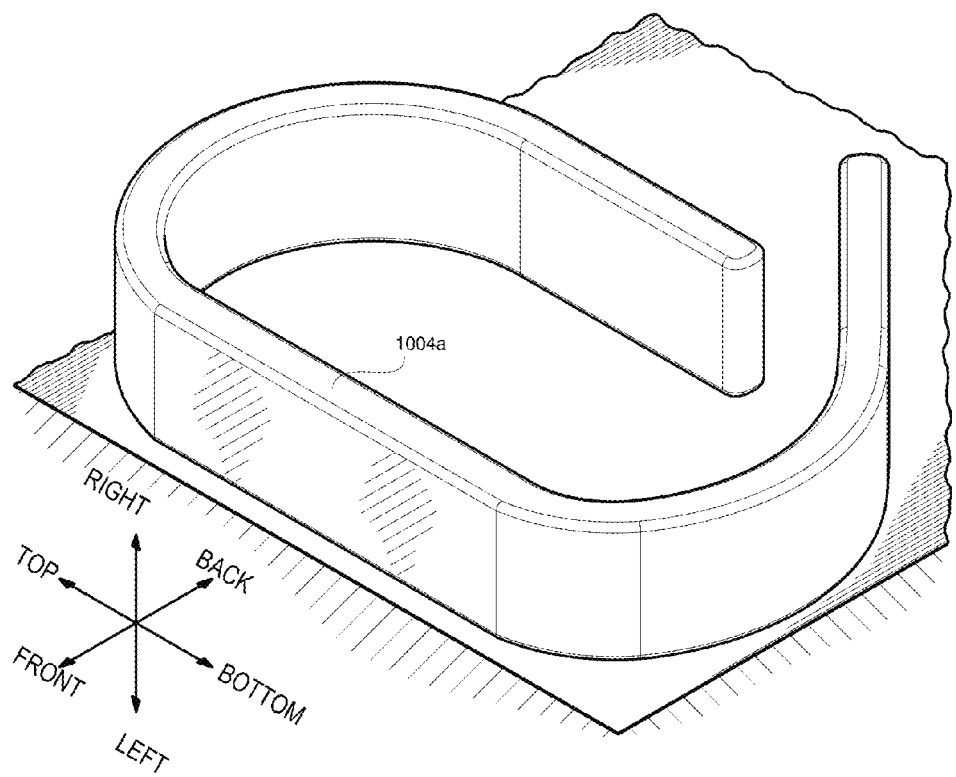
FIG. 10A illustrates a wearable electronic device placed on its side on a flat surface when not being worn according to one embodiment of the invention.
Figure 10B:
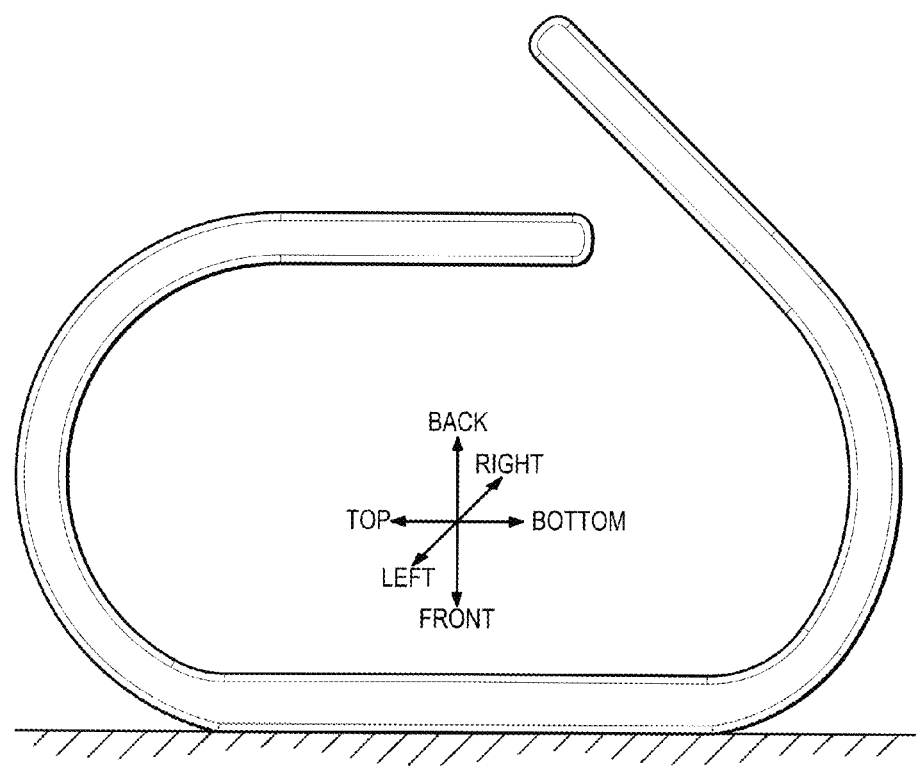
FIG. 10B illustrates a wearable electronic device placed on its face on a flat surface when not being worn according to one embodiment of the invention.
Figure 10C:
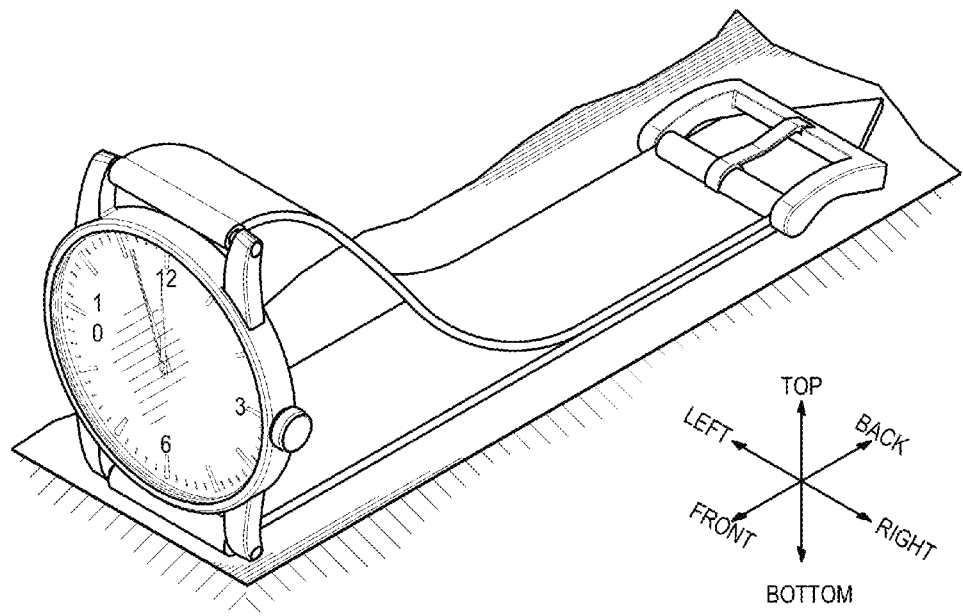
FIG. 10C illustrates a wearable electronic device placed on a flat surface such it is perpendicular to that flat surface when not being worn according to one embodiment of the invention.
Figure 10D:
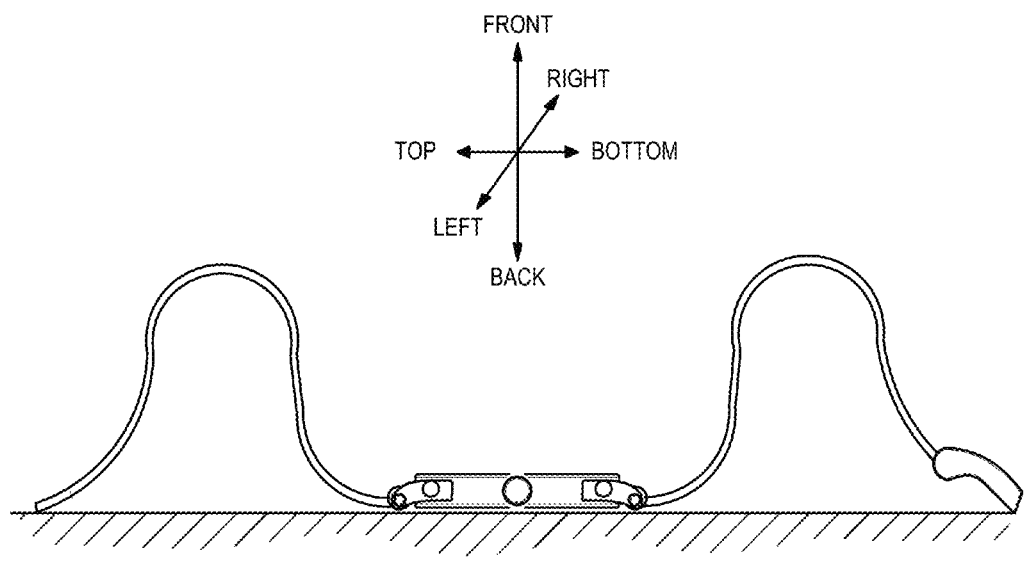
FIG. 10D illustrates a wearable electronic device being placed on its back on a flat surface when not being worn according to one embodiment of the invention.
Figure 10E:
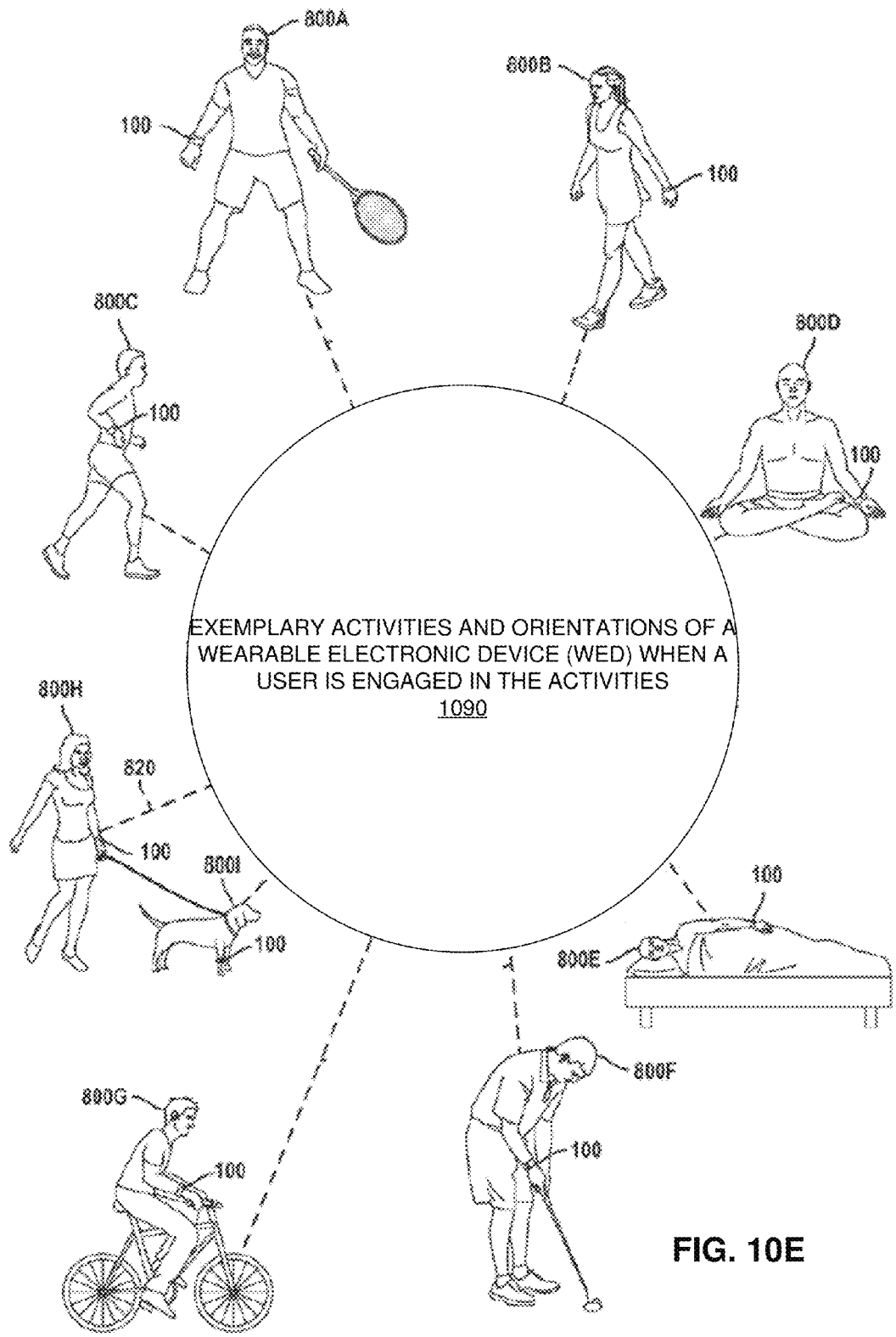
FIG. 10E illustrates orientations of a wearable electronic device when a user is engaged in various activities according to one embodiment of the invention.

FIGS. 10A-E illustrate orientations that different exemplary wearable electronic devices may be placed when not being worn according to embodiments, which may be represented by different not-worn profiles. FIGS. 10A-B illustrate a wearable electronic device having a C-shape and integrated housing and wristband according to one embodiment of the invention. FIGS. 10C-D illustrate a wearable electronic device having a wristband similar to a dress watchband, according to one embodiment of the invention. FIG. 10E illustrate a wearable electronic device worn by a user when the user is engaged in various activities according to embodiments. Note each depicted wearable electronic device in this set of figures may include an accelerometer.

FIG. 10A illustrates a wearable electronic device placed on its side on a flat surface when not being worn according to one embodiment of the invention. When placed in this orientation, the left-right axis (the Y-axis) runs substantially parallel to the force of gravity, and the acceleration along the left-right axis due to gravity will consistently meet a condition relative to a threshold acceleration expected along that axis when the wearable electronic device is in this orientation. While FIG. 10A illustrates the wearable electronic device on one of its sides, the wearable electronic device may also be commonly placed on its opposite side, such as on side 1004. Whether the wearable electronic device rests on the side shown in FIG. 10A or side 1004, gravity runs along the left-right axis, but in opposite directions. Thus, where the positive direction of the accelerometer measure from left to right, the acceleration data along the left-right axis may measure 1 g when the wearable electronic device is oriented as shown in FIG. 10A and but may measure −1 g when the wearable electronic device is oriented such that the wearable electronic device is on side 1004. As the wearable electronic device may rest on either side, the wearable electronic device may compare the detected acceleration data with either two different thresholds (one for each side (e.g., 1 g for the resting side shown in FIG. 10A and −1 g for the side 1004) or take the absolute value of the acceleration data from the left-right axis, which is then compared to a gravitational threshold (e.g., 1 g).

FIG. 10B illustrates a wearable electronic device resting on a face side on a flat surface when not being worn according to one embodiment. When placed in this orientation, the back-front axis (the Z-axis) runs substantially parallel to the force of gravity, and the acceleration along the back-front axis due to gravity meet a condition relative to a threshold acceleration expected along that axis when the wearable electronic device is in this orientation.

Note in one embodiment that it is very unlikely that the wearable electronic device will rest on its back when not being worn due to the shape and flexibility of the wristband forming the C-shape. Thus, FIGS. 10A-B illustrate the orientations that the wearable electronic device is commonly placed when not being worn.

FIG. 10C illustrates a wearable electronic device placed on a flat surface such that the face side of the wearable electronic device is perpendicular to that flat surface when not being worn according to one embodiment. When placed in this orientation, the top-bottom axis (the X-axis) runs substantially parallel to the force of gravity, and the acceleration along the top-bottom axis due to gravity will consistently meet a condition relative to a threshold acceleration expected along that axis when the wearable electronic device is in this orientation.

FIG. 10D illustrates a wearable electronic device being placed such that the back side is on a flat surface when not being worn according to one embodiment. When placed in this orientation, the back-front axis (the Z-axis) runs substantially parallel to the force of gravity, and the acceleration is along the back-front axis due to gravity will consistently meet a condition relative to a threshold acceleration expected along that axis when the wearable electronic device is in this orientation. The physical characteristics of the wearable electronic device FIG. 10D are such that it may also commonly be placed in the same orientation illustrated in FIG. 10B. Comparing FIG. 10D to FIG. 10B, the back-front axis runs in opposite directions relative to gravity. Thus, in an embodiment where the positive direction runs from back to front and the condition used for FIG. 10D is a determination whether the acceleration data is greater than a gravitational threshold, logically the condition for FIG. 10B would be a determination whether the acceleration data is less than a gravitational threshold. Of course, in other embodiments, such logic can be accomplished differently, such as by taking the absolute value of the acceleration data and comparing the absolute value against the gravitational threshold.

In one embodiment, the threshold acceleration in FIGS. 10A-B is based on the force on a stationary object needed to counteract gravity and an acceptable degree of tilt; the tilt may be in one or more of the orientation the wearable electronic device is commonly placed in when not being worn and the object on which the wearable electronic device is resting. For example, in some embodiments, the threshold acceleration equals 1 g multiplied by cosine (X°), wherein X° is selected from the range 0-40°, and more specifically 25-35°, and in one particular embodiment it is 30° for at least the orientation in FIG. 10A. While embodiments may use the same degree for all of the orientations the wearable electronic device is commonly placed in when not worn, different embodiments may chose different degrees of tilt for different ones of the orientations.

FIGS. 10A-D illustrate a number of common orientations a wearable electronic device may be placed when not being worn, and that such orientation depend on characteristics of the wearable electronic device, including one or more of a shape, a flexibility, and a range of motion of a mechanism (e.g., the wristband) used to wear the wearable electronic device on the user's forearm in one embodiment. In addition, these orientations are a result of physical characteristics of the wearable electronic device that come into direct physical contact with an object (e.g., the flat surface) on which the wearable electronic is placed in one embodiment. For example, while FIGS. 10A-D illustrate the orientations of a wearable electronic device on a flat surface, some wearable electronic devices may be designed to be placed differently when not being worn, such as in a watch box with a sloped surface. Thus, the common orientations of a wearable electronic device when not being worn are device specific, and different embodiments would take into account such common orientation(s) for a given device when selecting one or more axes along which the force of gravity will cause the acceleration along those axes to consistently meet a condition relative to a threshold acceleration.

In contrast with the common orientations a wearable electronic device may be placed when not being worn, FIG. 10E illustrates orientations of a wearable electronic device when a user is engaged in various activities according to one embodiment of the invention. As illustrated, user 800A is playing active sports (e.g., tennis), user 800B is walking, user 800C is running, user 800D is practicing yoga, user 800E is sleeping, user 800F is playing leisure sports (e.g., golf), user 800G is riding a bicycle, user 800H is walking her pet, and user 800I, a pet, is walking along its master. All of the users are wearing a wearable electronic device 100, and all but the pet has the wearable electronic device 100 worn on the forearm. The pet has the wearable electronic device worn on the leg. Thus, the wearable electronic device is designed to be worn in a particular way, and the particular way is unlikely to include the wearable electronic device remaining in the one or more orientations the wearable electronic device is commonly placed when not being worn, for a threshold amount of time.

Referring back to FIG. 10E, when a user is active such as users 800A-800C and 800E-800I, the acceleration measured by the accelerometer varies dynamically over time, and it is easier to differentiate from a non-worn state. However, when a user is near stationary as users 800D and 800E, the acceleration measured by the accelerometer varies little and/or infrequently, making it is harder to differentiate when the wearable electronic device is not being worn.

Yet, even when the user is relatively stationary, it may be uncommon for the user to keep the wearable electronic device in the same/similar orientations that the wearable electronic device would be when not being worn. For example, assuming wearable electronic device 100 has the similar characteristics of the wearable electronic device illustrated in FIGS. 10A-B. When user 800D is sleeping, the wearable electronic device 100 is at the side of his body. Thus, for example, when sleeping it is very unlikely that the wearable electronic device will be in the orientation illustrated in FIG. 10A (on its side) for a long period of time. Thus, it may be determined that wearable electronic device 100 is in a not-worn state when the acceleration measured along with the left-right axis meets a condition relative to a threshold acceleration expected along that axis. For example, the condition may be that the acceleration is over 0.7 g or below −0.7 g along left-right axis for a determinable time period, such as 5 minutes straight.

The condition for making the determination of not-worn state may be chosen depending on the likelihood that the wearable electronic device when worn will be in the same orientation that the wearable electronic device is commonly placed when not being worn. For example, it is uncommon for the wearable electronic device to remain in the orientation in FIG. 10B when not being worn, but less so than the orientation in FIG. 10A (e.g., user 800D may sleep with the wearable electronic device face-down for a period of time). Thus, the condition for making the determination of not-worn state may be that the acceleration is below −0.7 g along the back-front axis for 30 minutes straight.

Figure 11:
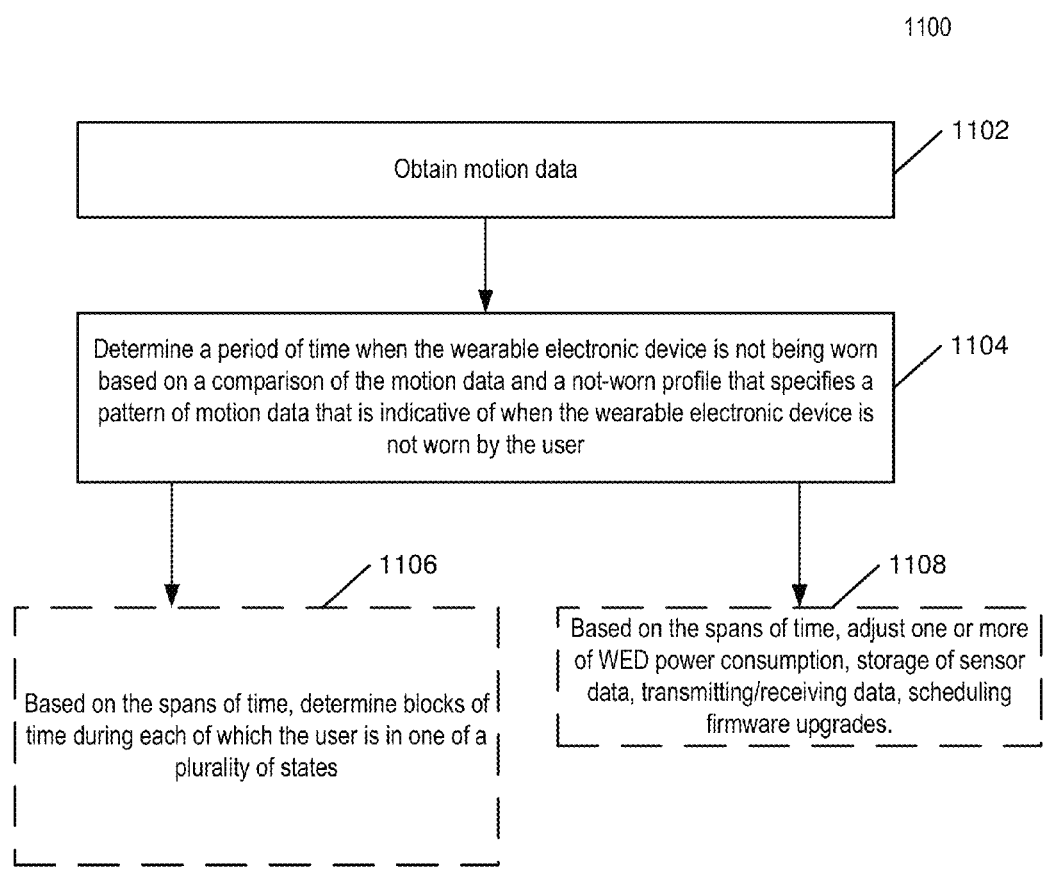
FIG. 11 is a flow diagram illustrating the automatic detection of when a wearable electronic device is not being worn based on an accelerometer according to one embodiment of the invention.

Flow Diagrams for Automatic Detection of when a Wearable Electronic Device is not being Worn Based on an Accelerometer FIG. 11 is a flow diagram illustrating the automatic detection of when a wearable electronic device is not being worn based on motion data, according to one embodiment. The method 1100 shown in FIG. 11 may be implemented in a wearable electronic device, or distributed between the wearable electronic device and another electronic device. The electronic device may be a server, a tablet, a smartphone (executing an application (referred to as an app)), a desktop, a laptop, a set top box, or any other computer device or computer system coupled to the wearable electronic device. In an example, references 1102 and 1108 may be performed on the WED, reference 1104 may be performed on the WED and/or another electronic device, and reference 1106 may be performed on another electronic device.

Operations of the method 1100 are now discussed. At reference 1102, the motion data is obtained via motion sensor of a wearable electronic device. As discussed above, the motion data can be accelerometer data (e.g., acceleration data along a single axis or along multiple axes) and the motion sensor can be an accelerometer (or accelerometers), a gyroscope, a gravity sensor, a rotation vector sensor, a location detection device (e.g., a GPS device, or a device capable of measuring movement using cell-phone or WiFi triangulation), or a magnetometer.

At reference 1104, the wearable electronic device may automatically determine a period of time when the wearable electronic device is not being worn based on a comparison of the motion data and a not-worn profile that specifies a pattern of motion data that is indicative of when the wearable electronic device is not worn by the user. In some cases, the not-worn profile may include a threshold value representing the force of gravity that is expected along an axis while the wearable electronic device rests in given orientation.

In one embodiment, the spans of time must be of a minimum length of time and is of a variable length of time, alternative embodiments implement fixed length spans of time. In one embodiment, the wearable electronic device is designed to be worn such that the display of the wearable electronic device is in the same place the display of a wrist watch would be located, the axis is parallel to the left-right axis of the display, and the orientation that the wearable electronic device is commonly placed when not being worn has the left-right axis substantially parallel to the gravitational force of the earth. The only acceleration measure used for purposes of making the automatic determinations is along one axis (also referred to herein as single axis) even though the accelerometer may be capable of measuring acceleration along multiple axes, alternative embodiments may operate differently. For example, in certain such alternative embodiments, the acceleration measure used for purposes of making different ones of the automatic determinations is along different ones of the axes (the acceleration along the axes are considered independently and different ones of the automatically determined spans of time will be based on the acceleration measure along only one of the axes). As another example, in certain such alternative embodiments, the acceleration measure used for purposes of making at least certain ones of the automatic determinations is along two or more of the axes (the acceleration along two or more of the axes are considered collectively and the automatically determined spans of time will be based on the acceleration measure along only the two or more of the axes—also referred to herein as collective axes). Different embodiments may implement different combinations of one or more single axis and collective axes; for example: 1) single axis to detect spans of time in a first orientation and collective axes for a second orientation; and 2) multiple single axis respectively for a first and second orientation, and collective axes for a third orientation.

Optionally at reference 1106, based on activity levels assigned to the spans of time, the wearable electronic device may assign a user state to blocks of time. Examples of user states include an awake state and an asleep state. In some cases, consecutive ones of the blocks of time have different states. In one embodiment, the spans of time assigned to the not worn activity state may result in the wearable electronic device assigning an awake state to a portion of a block of time that includes the span of times. However, other embodiments may operate differently. For example, the spans of time assigned to the not worn activity state may result in the wearable electronic device assigning an asleep state to a portion of a block of time that includes the span of times.

While in one embodiment reference 1106 may be performed as described earlier herein (and thus, the automatic detection of when a wearable electronic device is not being worn based on an accelerometer may be used in conjunction with the sleep tracker described earlier herein), reference 1106 may be performed using other sleep/awake state detection techniques.

Optionally at reference 1108, based on the spans of time, adjustments are made to one or more of the WED power consumption, storage of sensor data, transmission/receipt of data, and scheduling of firmware upgrades. For example, in one embodiment the WED power consumption is reduced during at least parts of the spans of time when the wearable electronic device is not being worn (e.g., reduce power consumed by one or more sensors by, for example, reducing their sensitivity or completely powering them down). As another example, in one embodiment the WED uses part of the spans of time to upload and/or download data from another electronic device.

Figure 12:
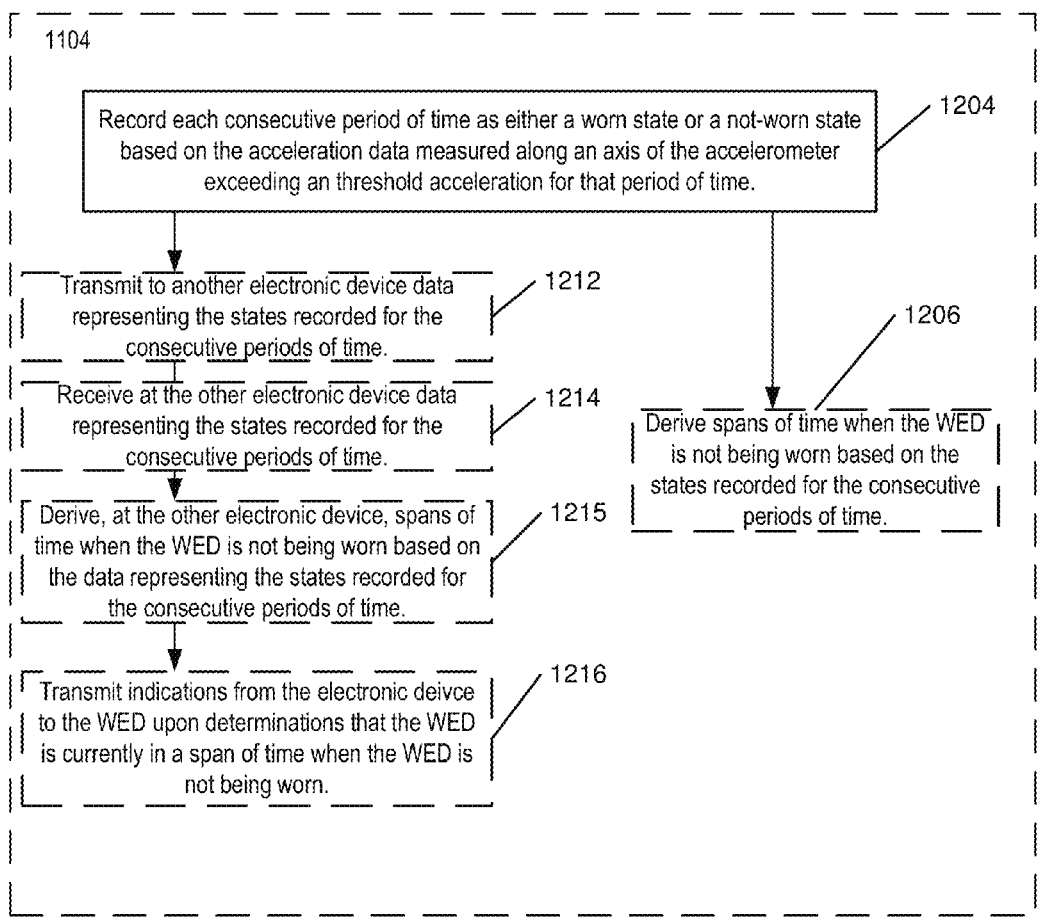
FIG. 12 illustrates exemplary alternative embodiments for implementing block 1104 from FIG. 11.

FIG. 12 illustrates exemplary alternative embodiments for implementing block 1104 from FIG. 11. While exemplary alternative embodiments are illustrated with reference to FIG. 12, it should be understood that other alternative embodiments are within the scope of the invention.

Reference 1204 illustrates the recordation of each consecutive period of time as either a worn state or a not-worn state based on the acceleration data measured along an axis of the accelerometer exceeding a threshold acceleration for that period of time. In one embodiment, reference 1204 is performed by the wearable electronic device. While in one embodiment the consecutive periods of time are non-overlapping, in alternative embodiments there may be some overlap. While in one embodiment of the invention the periods of time are of a fixed length, alternative embodiments may support variable length. While in one embodiment of the invention the periods of time are 30 seconds, alternative embodiments may select the period of time from within a range, for example, of 5-120 seconds. The one or more samples from the accelerometer along the axis during a given one of the periods of time are collectively represented by recording a single state (the worn state or the not—worn state) for that time period. This reduces data volume for processing, storage, and/or transmission. As such, the length of the periods of time are selected to sufficiently reduce data volume while preserving sufficiently meaningful data for subsequent operations described herein. Exemplary embodiments are discussed further herein with reference to FIG. 14A.

Further, while in one embodiment the times and states are recorded, in alternative embodiments the times and recorded states are compressed to form the data representing the states (e.g., where the periods of time are of a fixed length, the data may include a start time followed by a stream of 1s and zeros that each represent the state during one of the time periods; additional compression may also be performed (such as run length encoding)).

With regard to the above discussed exemplary use of one or more single axis and collective axes, in one embodiment separate states are recorded for each of the one or more single axis and collective axes used. For example, in an embodiment that only uses a single axis, there would be a single stream of recorded states for that axis. In contrast, in an embodiment that used two or more single axis, there would be a separate stream of recorded states for each of those single axis. As another example, in an embodiment that uses one or more collective axes, there would be a separate stream of recorded states for each of the collective axes.

While in one of the exemplary embodiments flow passes from reference 1204 to 1206 (reference 1206 being performed by the WED), in an alternative one of the exemplary embodiments flow passes from reference 1206 to references 1212-1216 (reference 1212 being performed by the WED and references 1214-1216 being performed in another electronic device ((e.g., server (including hardware and software)/tablet/smartphone containing an application (referred to as an app)) coupled to the wearable electronic device).

Reference 1206 illustrates the derivation of spans of time when the WED is not being worn based on the states recorded for the consecutive periods of time. In one embodiment, each of the spans of time includes at least a threshold consecutive number of the consecutive time periods recorded as the not-worn state. In one embodiment, reference 1206 is performed in real time and includes the detection of at least a threshold consecutive number of the consecutive time periods that were recorded as the not-worn state to derive the beginning of one of the spans of time (allowing reference 1108 to be performed). Exemplary implementations of reference 1206 are described further herein with reference to FIGS. 14A and 15A-B. While in one embodiment of the invention each of the spans of time must be of a minimum length of time (e.g., see FIGS. 15A-B) and is of a variable length of time, alternative embodiments implement fixed length spans of time.

Reference 1212 represents the transmission to another electronic device of data representing the states recorded for the consecutive periods of time. While in one embodiment the data representing the states includes times and the recorded states, in alternative embodiments the times and recorded states are compressed to form the data representing the states as described above.

Reference 1214 represents the receipt at the other electronic device of the data representing the states recorded for the consecutive periods of time. A variety of techniques may be used for implementing the communication represented by references 1212-1214, including wired/wireless and through one or more networks (including the Internet).

Reference 1215 illustrates the derivation of spans of time when the WED is not being worn based on the data representing the states recorded for the consecutive periods of time. Reference 1215 may be performed in similar fashion to reference 1206, or in a more advanced fashion where the other electronic device has more processing power and storage.

Optional reference 1216 illustrates the transmission of indications from the other electronic device to the WED upon determinations that the WED is currently in a span of time when the WED is not being worn. The transmissions of reference 1216 are utilized in one embodiment of the invention by the WED to perform reference 1108.

Operations Relating to Automatic Not-Worn State Detection

Figure 13:
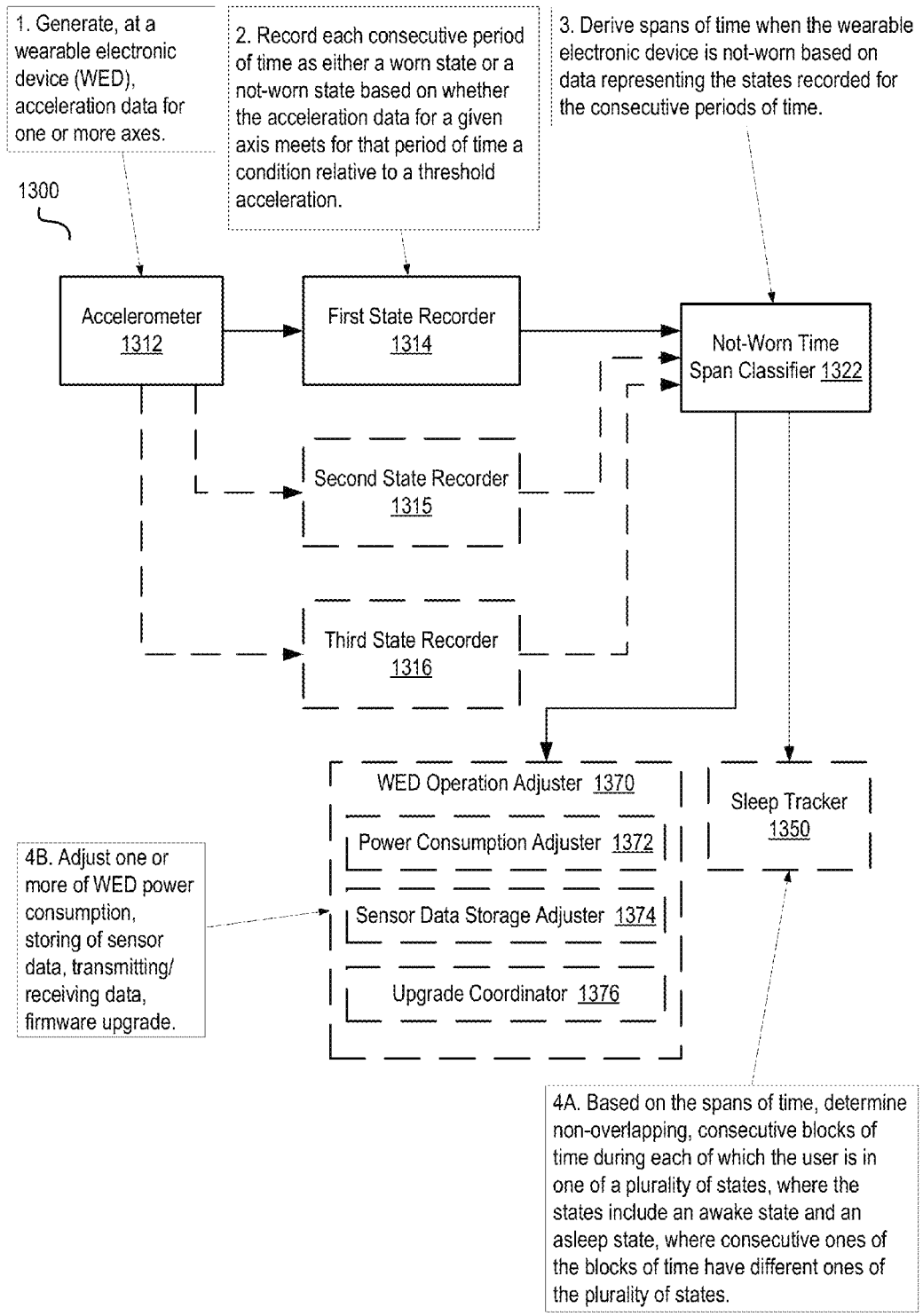
FIG. 13 illustrate operations relating to not-worn state detection utilizing accelerometer measures according to one embodiment of the invention.

FIG. 13 illustrate operations relating to not-worn state detection utilizing accelerometer measures according to one embodiment of the invention. The task boxes and blocks of FIG. 13 may be implemented in a wearable electronic device, or distributed between the wearable electronic device and one or more other electronic devices coupled to the wearable electronic device, where the one or more other electronic devices may, for example, be an electronic device (e.g., server (including hardware and software)/tablet/smartphone containing an application (referred to as an app)) to implement blocks 1322/1350. Task boxes 1-4 illustrate the order in which operations are performed by the components shown by blocks 1312-1370 according to one embodiment of the invention. It is to be appreciated that although the foregoing is discussed with reference to an accelerometer and acceleration data, other embodiments may utilize other types of motion sensors and motion data.

At task box 1, accelerometer 1312 generates acceleration data for one or more axes. For example, the acceleration may be sampled at 20 Hz for an axis, which is one sample every 0.05 seconds for that axis. When accelerometer 1312 generates the acceleration data only for one axis, the data will be forwarded to first state recorder 1314 and the second state recorder 1315 and third state recorder 1316 will not be utilized (or even present). When the acceleration data is generated for multiple axes, and the acceleration data for the multiple axes is to be used for the automatic not-worn state detection, one or more other state recorders (e.g., second recorder 1315 and third state recorder 1316) may be utilized.

At task box 2, one or more state recorders record each consecutive period of time as either a worn state or a not-worn state based on whether the acceleration data for a given axis meets for that period of time meets a condition relative to a threshold acceleration. In one embodiment, each state recorder operates in similar fashion as described in relation to reference 1204. That is, each recorder may compare the motion data for a given axis with a not-worn profile. As discussed herein above, one state recorder may record the periods of time based on acceleration data for single axis or collective axes.

As discussed above, the threshold accelerations for different state recorders may have different values. For example, a threshold acceleration for a common orientation A for not worn (e.g., the Y-axis as discussed relating to FIG. 10A) may be higher than the threshold acceleration for another common orientation B (e.g., the X-axis as discussed herein relating to FIG. 10C), as the common orientation A results in the Y-axis running closer to parallel to the force of gravity than the common orientation B results in the X-axis running parallel to the force of gravity for example. In that case, the state recorder corresponding to common orientation A may have a higher threshold acceleration than the one corresponding to common orientation B.

Figure 15A:
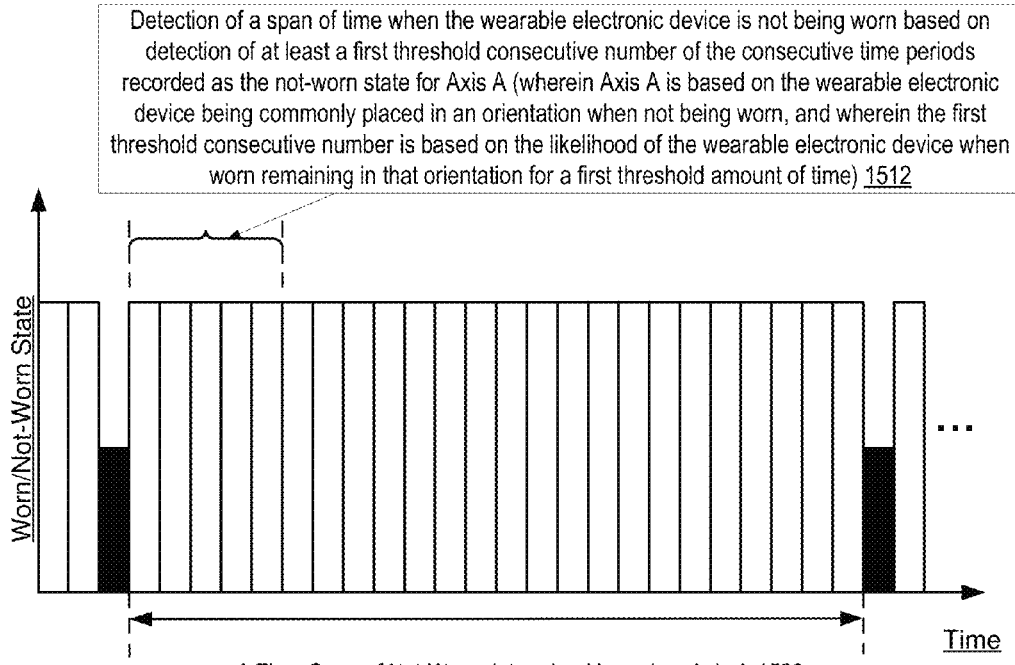
FIG. 15A illustrates detection of a span of time being in a not-worn state for a first axis according to one embodiment of the invention.
Figure 15B:
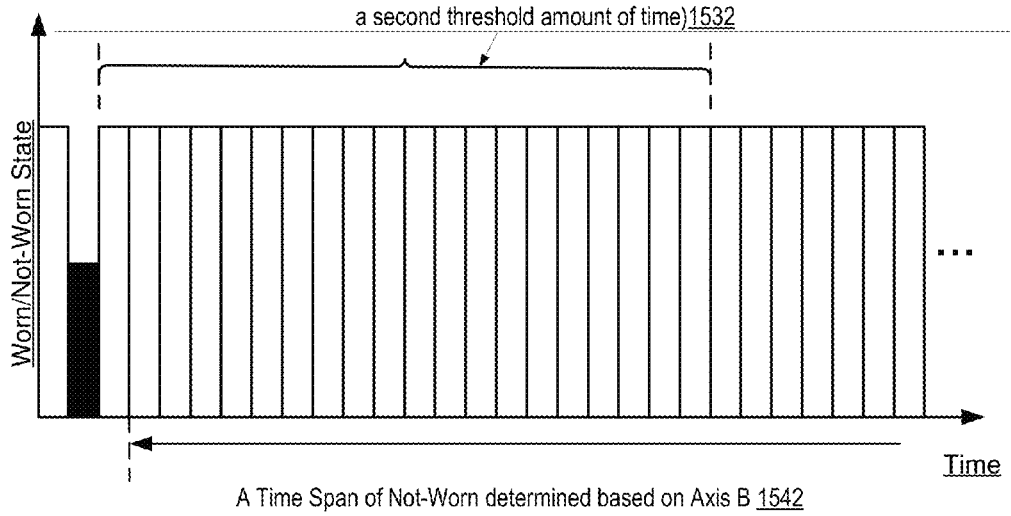
FIG. 15B illustrates detection of a span of time being in a not-worn state for a second axis according to one embodiment of the invention.

Then at task box 3, not-worn time span classifier 1322 derives spans of time when the wearable electronic device is not-worn based on data representing the states recorded for the consecutive periods of time. The various ways to derive the spans of time are discussed herein above for example in relation to FIG. 12 references 1206 and 1215. Note the threshold consecutive number of the consecutive time periods recorded as the not-worn state for one axis may be different for different ones of the state recorders as illustrated in FIGS. 15A-B.

Note that the state recorders and the not-worn time span classifiers utilize various thresholds (e.g., threshold acceleration and threshold consecutive number of the consecutive time periods recorded as the not-worn state), and these threshold may be different for different common orientations of the wearable electronic device when not being worn, as may be specified by different not-worn profiles.

Optionally at task box 4A, based on the spans of time, sleep tracker 1350 determines blocks of time (possibly non-overlapping and/or consecutive) during each of which the user is in one of a plurality of states, where the states include an awake state and an asleep state, where consecutive ones of the blocks of time have different ones of the plurality of states. Task box 4A may be implemented the various ways described in relation to reference 1106.

Also optionally at task box 4B, WED operation adjuster 1370 adjusts one or more of the WED power consumption, storage of sensor data, transmission/receipt of data, and scheduling of firmware upgrades. Task box 4B may be implemented the various ways described in relation to reference 1108.

Figure 14A:
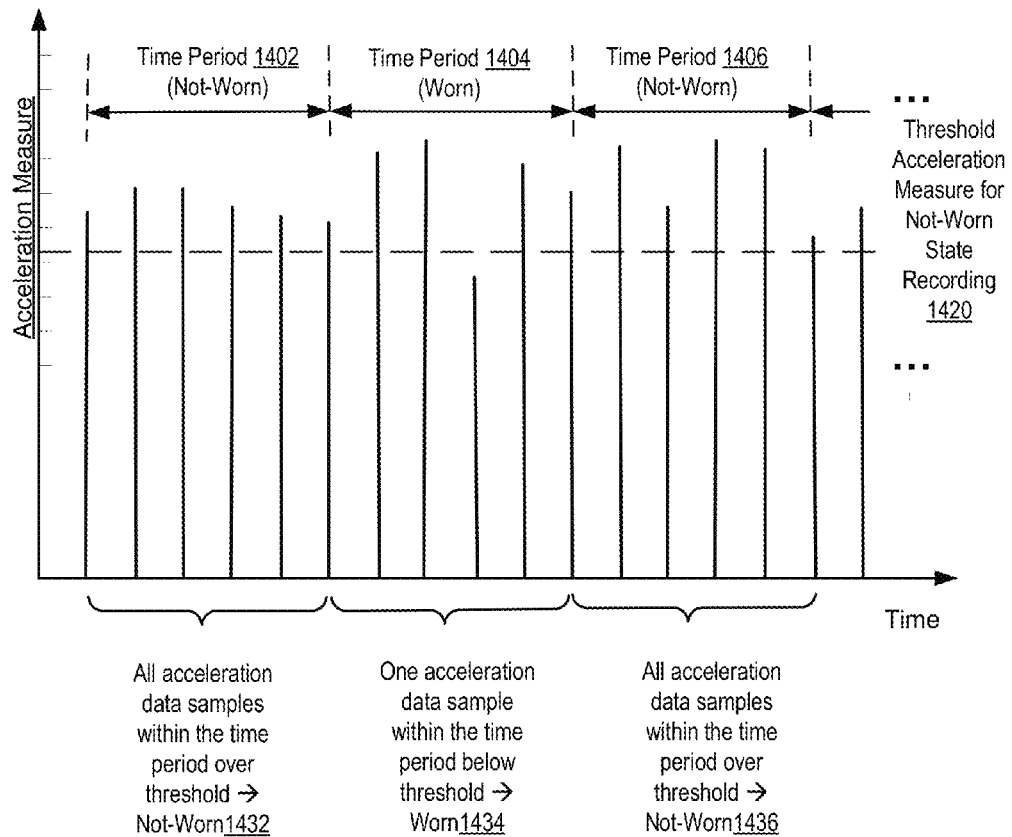
FIG. 14A illustrates the recordation of consecutive period of time as either a worn state or a not-worn state based on acceleration data measured along an axis of an accelerometer exceeding a threshold acceleration for that period of time according to one embodiment of the invention.

FIG. 14A illustrates the recordation of consecutive periods of time as either a worn state or a not-worn state based on acceleration data measured along an axis of an accelerometer exceeding a threshold acceleration for that period of time according to one embodiment of a not-worn state. In each time period 1402-1406, a number of acceleration data samples are generated for the axis, and each acceleration sample is compared with a threshold acceleration used for recording not-worn state (reference 1420). In this example, a time period is recorded as in a not-worn state when values of all the samples in the time period are over the threshold acceleration. To illustrate, the sampled acceleration at references 1432 and 1436 all exceed the threshold acceleration, and, thus, the time periods 1402 and 1406 are recorded as not-worn periods. In contrast, one value of the acceleration data in time period 1404 is below the threshold acceleration, and time period 1404 is recorded as worn state. The implementation of recording a not-worn state only if all the acceleration data is over the threshold can be used to reduce incorrectly detecting the not-worn state (false alarms).

Figure 14B:
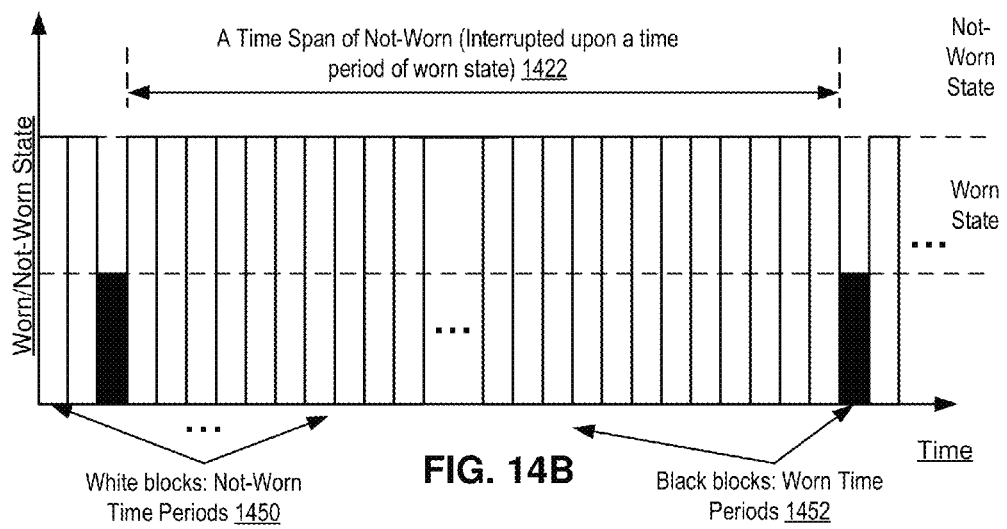
FIG. 14B illustrates the derivation of spans of time when a wearable electronic device is not being worn based on the states recorded for consecutive periods of time according to one embodiment of the invention.

FIG. 14B illustrates the derivation of spans of time when a wearable electronic device is not being worn based on the states recorded for consecutive periods of time according to one embodiment of the invention. The recorded states for the time periods are illustrated in the figure, where each time period is recorded as either worn (black block) or not-worn (white blocks) state. A time span of not worn includes consecutive time periods that the wearable electronic device is recorded as not-worn. As illustrated, time span at reference 1422 ends at the occurrence of a single time period of worn state. Note the span of time has to be long enough (over a threshold value of consecutive time periods) for a span of time of not-worn to be detected. If a set of consecutive time periods recorded as not-worn is interrupted prior to reaching the threshold, the span of time is derived as a worn state.

The threshold time period may, for example, be chosen from the range 5 minutes-2 hours. Also, the threshold time period may be different for different ones of the common orientations: for example, for a first one of the common orientations (e.g., FIG. 10A) the threshold time is chosen from the range 5 minutes to 120 minutes (e.g., 30 minutes), while for a second one of the common orientations (e.g., FIG. 10B) the range is 10 to 180 minutes (e.g., 60 minutes).

FIG. 15A illustrates detection of a span of time being in a not-worn state for a first axis according to one embodiment of the invention. In that embodiment, the span of time being in a not-worn state may not have a fixed length and it extends as long as there is not a worn state time period detected. It is advantageous to be able to detect a span of time when the wearable electronic device is not being worn, so that information may be used to for example to adjust operations of the wearable electronic device as discussed herein above. That detection, as illustrated in reference 1512, is based on detection of at least a first threshold consecutive number of the consecutive time periods recorded as the not-worn state for the first axis. The first axis is based on the wearable electronic device being commonly placed in an orientation when not being worn, and the first threshold consecutive number is based on the likelihood of the wearable electronic device when worn remaining in that orientation for a first threshold amount of time.

FIG. 15B illustrates detection of a span of time being in a not-worn state for a second axis according to one embodiment of the invention. That detection, as illustrated in reference 1522, is based on detection of at least a second threshold consecutive number of the consecutive time periods recorded as the not-worn state for the second axis. The second axis is based on the wearable electronic device being commonly placed in an orientation when not being worn, and the second threshold consecutive number is based on the likelihood of the wearable electronic device when worn remaining in that orientation for a second threshold amount of time. That is, the detection of the span of time being in a not-worn state for different axes may be based on different thresholds of consecutive number of time periods.

Figure 16:
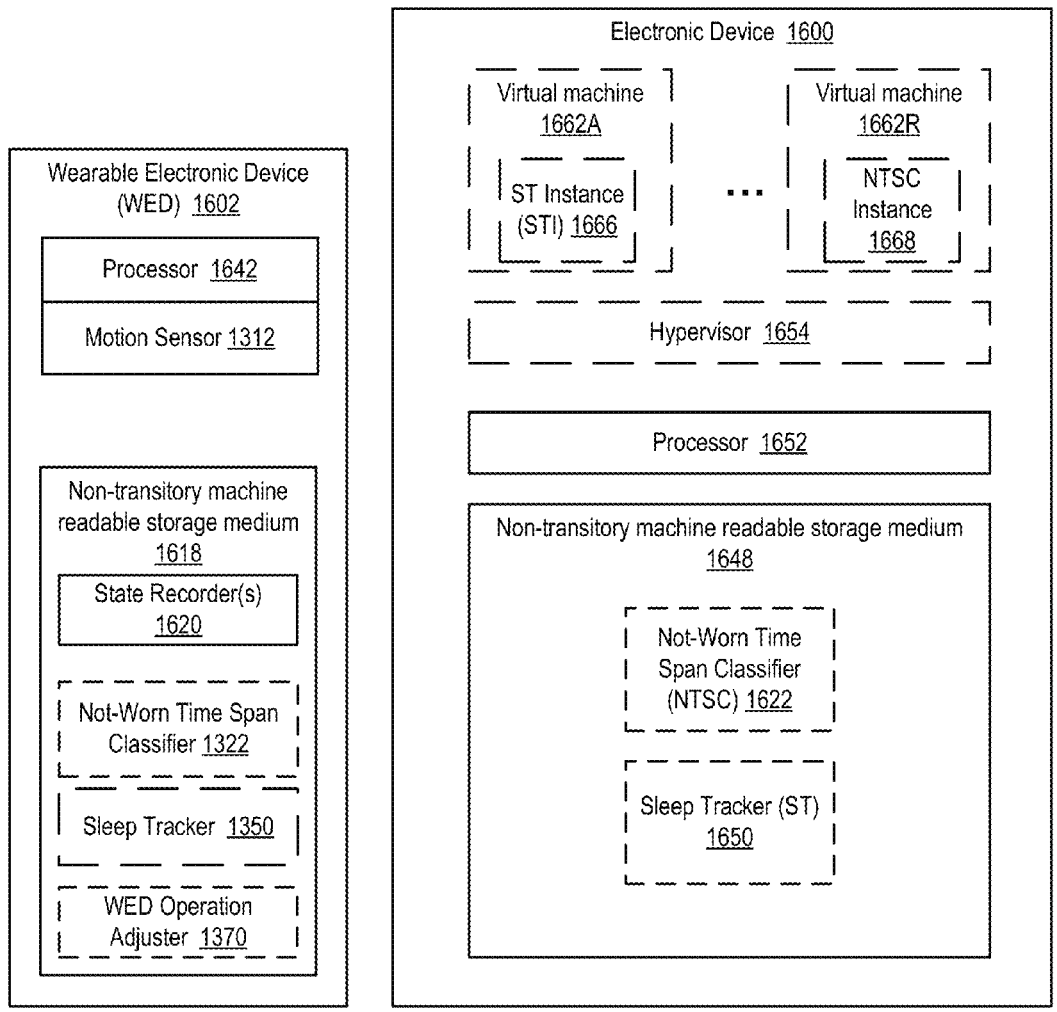
FIG. 16 is a block diagram illustrating the wearable electronic device and an electronic device implementing operations disclosed according to one embodiment of the invention.

Exemplary Devices Implementing Embodiments of Automatic Detection of Not-Worn State As previously described, while in some embodiments the operations are implemented in a wearable electronic device, alternative embodiments distribute different ones of the operations to different electronic devices (FIG. 16 illustrates examples of one such distribution). FIG. 16 is a block diagram illustrating the wearable electronic device and an electronic device implementing operations disclosed according to one embodiment of the invention. Wearable electronic device (WED) 1602 and electronic device 1600 are similar to WED 902 and electronic device 900 respectively, and the same or similar references indicate elements or components having the same or similar functionalities.

WED 1602 includes motion sensor(s) 1312 to generate motion data, such as acceleration data. It also has non-transitory machine readable storage medium 1618, which contains one or more state recorders 1620 as discussed herein above. The non-transitory machine readable storage medium 1618 may also include a not-worn time span classifier 1322 to classify when the derivation of spans of time being in a not-worn state. Similarly, the non-transitory machine readable storage medium 1618 may also include a sleep tracker 1350 and a WED operation adjuster 1370 when the associated operations are performed in the WED.

Electronic device 1600 has non-transitory machine readable storage medium 1648, which optionally contains not-worn time span classifier 1622 to classify when the derivation of spans of time being in a not-worn state is performed at electronic device 1600; and it contains sleep tracker 1650 when the determining of the user states, including awake and sleep states, is performed at electronic device 1600. In one embodiment, the sleep tracker 1650 is the sleep tracking module 950 of FIG. 9.

When executed by processor 1652, NTSC 1622 causes electronic device 1600 to perform the corresponding operations discussed herein above. Electronic device 1600 may contain virtual machines (VMs) 1662A to 1662R, each of which may execute a software instance of NTSC 1622. Hypervisor 1654 may present a virtual operating platform for the virtual machines 1662A to 1662R.

While the flow diagrams in the figures herein above show a particular order of operations performed by certain embodiments, it should be understood that such order is exemplary (e.g., alternative embodiments may perform the operations in a different order, combine certain operations, overlap certain operations, etc.).

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

Alternative Embodiments

Numerous specific details have been set forth herein. However, it is to be understood that embodiments may be practiced without these specific details. In other instances, well-known circuits, structures and techniques have not been shown in detail in order not to obscure the understanding of this description. It will be appreciated, however, by one skilled in the art that the invention may be practiced without such specific details. Those of ordinary skill in the art, with the included descriptions, will be able to implement appropriate functionality without undue experimentation.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Bracketed text and blocks with dashed borders (e.g., large dashes, small dashes, dot-dash, and dots) may be used herein to illustrate optional operations that add additional features to embodiments. However, such notation should not be taken to mean that these are the only options or optional operations, and/or that blocks with solid borders are not optional in certain embodiments.

In this description and following claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other. A "set," as used herein refers to any positive whole number of items including one item.

The operations in the flow diagrams have been described with reference to the exemplary embodiments of the other figures. However, it should be understood that the operations of the flow diagrams can be performed by embodiments other than those discussed with reference to the other figures, and the embodiments discussed with reference to these other figures can perform operations different than those discussed with reference to the flow diagrams.

The following lists some alternative embodiments, by way of example and not limitation.

Embodiment 31. An apparatus for automatically detecting periods of sleep of a user of a wearable electronic device, the apparatus comprising: a set of one or more processors; a non-transitory machine readable storage medium coupled to the set of one or more processors and having stored therein instructions, which when executed by the set of one or more processors, cause the apparatus to: obtain a set of features for one or more periods of time from motion data obtained from a set of one or more motion sensors or data derived therefrom; classify the one or more periods of time as one of a plurality of statuses of the user based on the set of features determined for the one or more periods of time, wherein the statuses are indicative of relative degree of movement of the user, and derive blocks of time covering the period of time during which the user is in one of a plurality of states, wherein the states include an awake state and an asleep state.

Embodiment 32. The apparatus of embodiment 31, wherein the classification is performed using a machine learning classifier.

Embodiment 33. The apparatus of embodiment 31, wherein the plurality of statuses further include a not-worn status, during which the user is not wearing the wearable electronic device.

Embodiment 34. The apparatus of embodiment 31, wherein the apparatus is one of the wearable electronic device and a secondary electronic device is coupled to the wearable electronic device.

Embodiment 35. The apparatus of embodiment 33, wherein the combination of the quantification of the distribution of the motion data comprises a combination of a statistical measure of the motion data along each of the three axes.

Embodiment 36. The apparatus of embodiment 31, wherein the classification of each of the periods of time is further based on photoplethysmography (PPG) data from a time window that includes that period of time, and wherein the PPG data is generated by a photoplethysmographic sensor in the wearable electronic device.

Embodiment 37. The apparatus of embodiment 36, wherein the PPG data is utilized to calculate at least one of the user's: heart rate data; heart rate variability data; and respiration data.

Embodiment 38. The apparatus of embodiment 31, wherein the instructions, when executed by the set of processors, also cause the apparatus further to: after the derivation of the user being in an asleep state, determine, for the periods of time at which the user is in the asleep state, another set of one or more statistical features of which at least one characterizes a distribution of movement of the user, and classify each of the periods of time into a plurality of sleep stages of the user based on the set of statistical features determined for that moment of interest, wherein the sleep stages include a rapid eye movement (REM) stage and a plurality of non-REM stages.

Embodiment 39. The apparatus of embodiment 31, wherein the classification of each of the periods of time is further based on data generated by a set of additional sensors in the wearable electronic device, wherein the set includes one or more of the following: temperature sensor; ambient light sensor; galvanic skin response sensor; capacitive sensor; humidity sensor; and sound sensor.

Embodiment 40. The apparatus of embodiment 31, wherein the set of motion sensors include an accelerometer.

Embodiment 41. A method comprising: obtaining a set of features for one or more periods of time from motion data obtained from a set of one or more motion sensors or data derived therefrom; classifying the one or more periods of time as one of a plurality of statuses of the user based on the set of features determined for the one or more periods of time, wherein the statuses are indicative of relative degree of movement of the user; and deriving blocks of time covering the period of time during which the user is in one of a plurality of states, wherein the states include an awake state and an asleep state.

Embodiment 42. The method of embodiment 41, wherein the classification is performed using a machine learning classifier.

Embodiment 43. The method of embodiment 41, wherein the plurality of statuses further include a not-worn status, during which the user is not wearing the wearable electronic device.

Embodiment 44. The method of embodiment 41, wherein the apparatus is one of the wearable electronic device and a secondary electronic device is coupled to the wearable electronic device.

Embodiment 45. The method of embodiment 43, wherein the combination of the quantification of the distribution of the motion data comprises a combination of a statistical measure of the motion data along each of the three axes.

Embodiment 46. The method of embodiment 41, wherein the classification of each of the periods of time is further based on photoplethysmography (PPG) data from a time window that includes that period of time, and wherein the PPG data is generated by a photoplethysmographic sensor in the wearable electronic device.

Embodiment 47. The method of embodiment 46, wherein the PPG data is utilized to calculate at least one of the user's: heart rate data; heart rate variability data; and respiration data.

Embodiment 48. The method of embodiment 41, wherein the instructions, when executed by the set of processors, also cause the apparatus further to: after the derivation of the user being in an asleep state, determining, for the periods of time at which the user is in the asleep state, another set of one or more statistical features of which at least one characterizes a distribution of movement of the user, and classifying each of the periods of time into a plurality of sleep stages of the user based on the set of statistical features determined for that moment of interest, wherein the sleep stages include a rapid eye movement (REM) stage and a plurality of non-REM stages.

Embodiment 49. The method of embodiment 41, wherein the classification of each of the periods of time is further based on data generated by a set of additional sensors in the wearable electronic device, wherein the set includes one or more of the following: temperature sensor; ambient light sensor; galvanic skin response sensor; capacitive sensor; humidity sensor; and sound sensor.

Embodiment 50. The method of embodiment 41, wherein the set of motion sensors include an accelerometer.

Embodiment 51. A computer readable storage device that includes instructions that, when executed by one or more processors, cause the one or more processors to: obtain a set of features for one or more periods of time from motion data obtained from a set of one or more motion sensors or data derived therefrom; classify the one or more periods of time as one of a plurality of statuses of the user based on the set of features determined for the one or more periods of time, wherein the statuses are indicative of relative degree of movement of the user; and derive blocks of time covering the period of time during which the user is in one of a plurality of states, wherein the states include an awake state and an asleep state.

Embodiment 52. The computer readable storage device of embodiment 51, wherein the classification is performed using a machine learning classifier.

Embodiment 53. The computer readable storage device of embodiment 51, wherein the plurality of statuses further include a not-worn status, during which the user is not wearing the wearable electronic device.

Embodiment 54. The computer readable storage device of embodiment 51, wherein the apparatus is one of the wearable electronic device and a secondary electronic device is coupled to the wearable electronic device.

Embodiment 55. The computer readable storage device of embodiment 53, wherein the combination of the quantification of the distribution of the motion data comprises a combination of a statistical measure of the motion data along each of the three axes.

Embodiment 56. The computer readable storage device of embodiment 51, wherein the classification of each of the periods of time is further based on photoplethysmography (PPG) data from a time window that includes that period of time, and wherein the PPG data is generated by a photoplethysmographic sensor in the wearable electronic device.

Embodiment 57. The computer readable storage device of embodiment 56, wherein the PPG data is utilized to calculate at least one of the user's: heart rate data; heart rate variability data; and respiration data.

Embodiment 58. The computer readable storage device of embodiment 51, wherein the instructions, when executed by the set of processors, also cause the apparatus further to: after the derivation of the user being in an asleep state, determine, for the periods of time at which the user is in the asleep state, another set of one or more statistical features of which at least one characterizes a distribution of movement of the user, and classify each of the periods of time into a plurality of sleep stages of the user based on the set of statistical features determined for that moment of interest, wherein the sleep stages include a rapid eye movement (REM) stage and a plurality of non-REM stages.

Embodiment 59. The computer readable storage device of embodiment 51, wherein the classification of each of the periods of time is further based on data generated by a set of additional sensors in the wearable electronic device, wherein the set includes one or more of the following: temperature sensor; ambient light sensor; galvanic skin response sensor; capacitive sensor; humidity sensor; and sound sensor.

Embodiment 60. The computer readable storage device of embodiment 51, wherein the set of motion sensors include an accelerometer.

Embodiment 61. A wearable electronic device to be worn by a user, the wearable electronic device comprising: a set of sensors that detects physiological data or environmental data of the user; a set of one or more processors coupled to the set of sensors; and a non-transitory machine readable storage medium coupled to the set of one or more processors and having stored therein instructions, which when executed by the set of one or more processors, cause the wearable electronic device to: based on detecting that a state of the user, as tracked by the wearable electronic device, has transitioned into an asleep state, decrease power consumption of at least one sensor from the set of sensors, and based on detecting that the state of the user, as tracked by the wearable electronic device, has transitioned out of the asleep state, reverse the decrease of power consumption of the at least one sensor.

Embodiment 62. The wearable electronic device of embodiment 61, wherein the set of sensors includes a photoplethysmographic sensor to generate photoplethysmography (PPG) data of the user, wherein the photoplethysmographic sensor includes a light source and a photodetector.

Embodiment 63. The wearable electronic device of embodiment 62, wherein the decrease of the power consumption includes at least one of: decrease of a sampling rate of the photoplethysmographic sensor, decrease of sensitivity of the photoplethysmographic sensor, and decrease of a power level of the light source.

Embodiment 64. The wearable electronic device of embodiment 62, wherein the instructions, when executed by the set of processors, also cause the wearable electronic device to: after the decrease, increasing the power consumption of the photoplethysmographic sensor to generate additional PPG data for sleep stage detection.

Embodiment 65. The wearable electronic device of embodiment 64, wherein the increase of power consumption of the photoplethysmographic sensor includes at least one of: increase of a sampling rate of the photoplethysmographic sensor, increase of sensitivity of the photoplethysmographic sensor, and increase of a power level of the light source.

Embodiment 66. The wearable electronic device of embodiment 61, wherein the set of sensors includes a motion sensor to generate motion data of the user.

Embodiment 67. The wearable electronic device of embodiment 66, wherein the decrease of the power consumption includes at least one of: entering a low precision state of the motion sensor, decrease sensitivity of the motion sensor, and decrease of a sampling rate of the motion sensor.

Embodiment 68. The wearable electronic device of embodiment 66, wherein the motion sensor is an accelerometer.

Embodiment 69. The wearable electronic device of embodiment 66, wherein the instructions, when executed by the set of processors, also cause the wearable electronic device to: after the decrease and before the reverse, periodically temporarily increase the power consumption of the motion sensor to generate additional motion data for sleep stage detection.

Embodiment 70. The wearable electronic device of embodiment 69, wherein the increase of power consumption of the motion sensor includes at least one of: entering a high precision state of the motion sensor, increase of sensitivity of the motion sensor, and increase of a sampling rate of the motion sensor.

Embodiment 71. A wearable electronic device to be worn by a user, the wearable electronic device comprising: a set of sensors including at least one of: a photoplethysmographic (PPG) sensor to generate PPG data of the user, wherein the photoplethysmographic sensor includes a light source and a photodetector, a motion sensor to generate motion data of the user; a set of one or more processors coupled to the photoplethysmographic sensor; a non-transitory machine readable storage medium coupled to the set of one or more processors and having stored therein instructions, which when executed by the set of one or more processors, cause the wearable electronic device to: based on motion data generated by the motion sensor, determine that the user is sleeping; responsive to the determination that the user is sleeping, increase power consumption of at least one of the photoplethysmographic sensor and the motion sensor, based on motion data generated by the motion sensor, determine that the user is awake; and responsive to the determination that the user is awake, reverse the increase of power consumption of the at least one of the photoplethysmographic sensor and the motion sensor.

Embodiment 72. The wearable electronic device of embodiment 71, wherein the increase in power consumption generates increases PPG data generated by the PPG sensor, wherein the instructions, which when executed by the set of one or more processors, also causes the wearable electronic device to calculate at least one of: a set of heart rates of the user, a set of heart rate variabilities of the user, and a set of respiration rate of the user.

Embodiment 73. The wearable electronic device of embodiment 71, wherein the additional data is motion data used to generate movement measures at time intervals based on a combination of a quantification of a distribution of the motion data along each of the three axes during that time interval, and wherein each of the movement measures is a single numeric number.

Embodiment 74. The wearable electronic device of embodiment 71, wherein the increase of power consumption includes at least one of: increase of a sampling rate of the photoplethysmographic sensor, increase of sensitivity of the photoplethysmographic sensor, and increase of a power level of the light source.

Embodiment 75. The wearable electronic device of embodiment 71, wherein the increase of power consumption includes at least one of: entering a high precision state of the motion sensor, increase of sensitivity of the motion sensor, and increase of a sampling rate of the motion sensor.

Embodiment 76. The wearable electronic device of embodiment 71, wherein the light source is a light-emitting diode (LED).

Embodiment 78. A method of managing power consumption of a wearable electronic device, wherein the wearable electronic device includes a set of sensors, the method comprising: based on detecting that a state of the user, as tracked by the wearable electronic device, has transitioned into an asleep state, decrease power consumption of at least one sensor from the set of sensors; and based on detecting that the state of the user, as tracked by the wearable electronic device, has transitioned out of the asleep state, reverse the decrease of power consumption of the at least one sensor.

Embodiment 79. The wearable electronic device of embodiment 78, wherein the set of sensors includes a photoplethysmographic sensor to generate photoplethysmography (PPG) data of the user, wherein the photoplethysmographic sensor includes a light source and a photodetector.

Embodiment 80. The wearable electronic device of embodiment 79, wherein the decrease of the power consumption includes at least one of: decrease of a sampling rate of the photoplethysmographic sensor, decrease of sensitivity of the photoplethysmographic sensor, and decrease of a power level of the light source.

Embodiment 81. The wearable electronic device of embodiment 79, wherein the instructions, when executed by the set of processors, also cause the wearable electronic device to: after the decrease and before the reverse, periodically temporarily increase the power consumption of the photoplethysmographic sensor to generate additional PPG data for sleep stage detection.

Embodiment 82. The wearable electronic device of embodiment 81, wherein the increase of power consumption of the photoplethysmographic sensor includes at least one of: increase of a sampling rate of the photoplethysmographic sensor, increase of sensitivity of the photoplethysmographic sensor, and increase of a power level of the light source.

Embodiment 83. The wearable electronic device of embodiment 78, wherein the set of sensors includes a motion sensor to generate motion data of the user.

Embodiment 84. The wearable electronic device of embodiment 83, wherein the decrease of the power consumption includes at least one of: entering a low precision state of the motion sensor, decrease sensitivity of the motion sensor, and decrease of a sampling rate of the motion sensor.

Embodiment 85. The wearable electronic device of embodiment 83, wherein the instructions, when executed by the set of processors, also cause the wearable electronic device to: after the decrease and before the reverse, periodically temporarily increase the power consumption of the motion sensor to generate additional motion data for sleep stage detection.

Embodiment 86. The wearable electronic device of embodiment 85, wherein the increase of power consumption of the motion sensor includes at least one of: entering a high precision state of the motion sensor, increase of sensitivity of the motion sensor, and increase of a sampling rate of the motion sensor.

Embodiment 87. A method of managing power consumption of a wearable electronic device, wherein the wearable electronic device includes a set of sensors, including at least one of a photoplethysmographic sensor to generate photoplethysmography (PPG) data of the user, the photoplethysmographic sensor including a light source and a photodetector, and a motion sensor to generate motion data of the user, the method comprising: responsive to a state of the user, as tracked by the wearable electronic device, transitioning into an asleep state, increasing power consumption of the at least one of the photoplethysmographic sensor and the motion sensor, wherein the increase of power consumption provides additional data for sleep stage detection; and responsive to the state of the user, as tracked by the wearable electronic device, transitioning out of the asleep state, reversing the increase of power consumption of the at least one of the photoplethysmographic sensor and the motion sensor.

Embodiment 88. The method of embodiment 85, wherein the additional data is PPG data used to calculate at least one of: a set of heart rates of the user, a set of heart rate variabilities of the user, and a set of respiration rate of the user.

Embodiment 89. The method of embodiment 85, wherein the additional data is motion data used to generate movement measures at time intervals based on a combination of a quantification of a distribution of the motion data along each of the three axes during that time interval, and wherein each of the movement measures is a single numeric number.

Embodiment 90. The method of embodiment 85, wherein the increasing the power consumption includes at least one of: increase of a sampling rate of the photoplethysmographic sensor, increase of sensitivity of the photoplethysmographic sensor, and increase of a power level of the light source.

Embodiment 91. A wearable electronic device comprising: a set of one or more motion sensors to generate motion data; a set of one or more processors; and a non-transitory machine readable storage medium coupled to the motion sensor and the set of one or more processors, the non-transitory machine readable storage medium having stored therein instructions, which when executed by the set of processors, cause the set of processors to: automatically determine a period of time when the wearable electronic device is not being worn based on a comparison of the motion data and a not-worn profile that specifies a pattern of motion data that is indicative of when the wearable electronic device is not worn by the user, and store, in the non-transitory machine readable storage medium, data associating the period of time with a not-worn state.

Embodiment 92. The wearable electronic device of embodiment 91, wherein the motion data includes a number of motion data samples, and the instructions, when executed by the set of processors, cause the device to automatically determine that the wearable electronic device is not worn for the period of time based on causing the set of processors to: determine that a number of motion data samples failing to meet a motion measurement threshold is below a threshold number.

Embodiment 93. The apparatus of embodiment 91, wherein the non-transitory machine readable storage medium also stores additional data associating additional periods of time with the not-worn state, the period of time and the additional periods of time together representing consecutive periods of time, and wherein the instructions, when executed, also cause the set of processors to: derive a span of time covering the consecutive periods of time based on the data and the additional data associating consecutive periods of time with the not-worn state; and store, in the non-transitory machine readable storage medium, data associating the span of time with the not worn state.

Embodiment 94. The apparatus of embodiment 93, wherein the derivation of the span of time includes instructions that, when executed, cause the set of processors to: detect that the consecutive periods of time includes at least a threshold consecutive number of periods of time from the period of time and the additional periods of time that were associated with the not-worn state.

Embodiment 95. The apparatus of embodiment 91, wherein the instructions, when executed by the set of processors, also cause the wearable electronic device to: automatically cause, based on the not-worn state for the period of time, one or more of a reduction in power consumption of the wearable electronic device, a discontinuation of storage of sensor data from a set of one or more sensors of the wearable electronic device, a communication of data to another electronic device, and a receipt of a firmware update from another electronic device.

Embodiment 96. The apparatus of embodiment 91, wherein the instructions, when executed by the set of processors, also cause the set of processors to automatically determine another period of time when the wearable electronic device is not being worn based on a subsequent comparison of the motion data and another not-worn profile that specifies a different pattern of motion data that is indicative of when the wearable electronic device is not worn by the user.

Embodiment 97. The apparatus of embodiment 91, wherein the pattern of motion data characterizes an orientation of the wearable electronic device.

Embodiment 98. The apparatus of embodiment 97, wherein the pattern of motion data further characterizes an acceptable range of motion for the orientation.

Embodiment 99. The apparatus of embodiment 97, wherein the pattern of motion data characterizes the orientation based on a threshold force of acceleration along one or more axes consistent with a force of gravity being applied along the one or more axes.

Embodiment 100. The apparatus of embodiment 97, wherein the pattern of motion data characterizes the orientation based on a threshold force of acceleration along one or more axes consistent with a force of gravity being applied along the one or more axes.

Embodiment 101. The apparatus of embodiment 100, wherein the threshold force of acceleration accounts for a determinable degree of tilt by the wearable electronic device.

Embodiment 102. The apparatus of embodiment 99, wherein the one or more axes represents an axis running across a display.

Embodiment 103. The apparatus of embodiment 99, wherein the one or more axes represents an axis running through a display.

Embodiment 104. The apparatus of embodiment 91, wherein the instructions, when executed by the set of processors, also cause the set of processors to: transmit to another electronic device data representing the association of the not worn state and the period of time.

Embodiment 105. The apparatus of embodiment 91, wherein the instructions, when executed by the set of processors, also cause the set of processors to: automatically determine a subsequent period of time when the wearable electronic device is being worn based on a subsequent comparison of the motion data and the not-worn profile that specifies the pattern of motion data that is indicative of when the wearable electronic device is not worn by the user; and store, in the non-transitory machine readable storage medium, data associating the subsequent period of time with a worn state.

Embodiment 106. A method executed by a set of one or more processors of a wearable electronic device, the method comprising: obtaining motion data generated by a set of one or more motion sensors of the wearable electronic device; determining a period of time when the wearable electronic device is not being worn based on a comparison of the motion data and a not-worn profile that specifies a pattern of motion data that is indicative of when the wearable electronic device is not worn by the user; and storing, in a non-transitory machine readable storage medium of the wearable electronic device, data associating the period of time with a not-worn state.

Embodiment 107. The method of embodiment 106, wherein the motion data includes a number of motion data samples, and the determining that the wearable electronic device is not worn for the period of time includes: determining that a number of motion data samples failing to meet a motion measurement threshold is below a threshold number.

Embodiment 108. The method of embodiment 106, further comprising: storing, in the non-transitory machine readable storage medium, additional data associating additional periods of time with the not-worn state, the period of time and the additional periods of time together representing consecutive periods of time; deriving a span of time covering the consecutive periods of time based on the data and the additional data associating consecutive periods of time with the not-worn state; and storing, in the non-transitory machine readable storage medium, data associating the span of time with the not worn state.

Embodiment 109. The method of embodiment 108, wherein the deriving comprises: detecting that the consecutive periods of time includes at least a threshold consecutive number of periods of time from the period of time and the additional periods of time that were associated with the not-worn state.

Embodiment 110. The method of embodiment 106, further comprising: causing, based on the not-worn state for the period of time, one or more of a reduction in power consumption of the wearable electronic device, a discontinuation of storage of sensor data from a set of one or more sensors of the wearable electronic device, a communication of data to another electronic device, and a receipt of a firmware update from another electronic device.

Embodiment 111. The method of embodiment 106, further comprising: determining another period of time when the wearable electronic device is not being worn based on a subsequent comparison of the motion data and another not-worn profile that specifies a different pattern of motion data that is indicative of when the wearable electronic device is not worn by the user.

Embodiment 112. The method of embodiment 106, wherein the pattern of motion data characterizes an orientation of the wearable electronic device.

Embodiment 113. The method of embodiment 112, wherein the pattern of motion data further characterizes an acceptable range of motion for the orientation.

Embodiment 114. The method of embodiment 112, wherein the pattern of motion data characterizes the orientation based on a threshold force of acceleration along one or more axes consistent with a force of gravity being applied along the one or more axes.

Embodiment 115. The method of embodiment 112, wherein the pattern of motion data characterizes the orientation based on a threshold force of acceleration along one or more axes consistent with a force of gravity being applied along the one or more axes.

Embodiment 116. The method of embodiment 115, wherein the threshold force of acceleration accounts for a determinable degree of tilt by the wearable electronic device.

Embodiment 117. The method of embodiment 114, wherein the one or more axes represents an axis running across a display.

Embodiment 118. The method of embodiment 114, wherein the one or more axes represents an axis running through a display.

Embodiment 119. The method of embodiment 106, further comprising: transmitting to another electronic device data representing the association of the not worn state and the period of time.

Embodiment 120. The method of embodiment 106, further comprising: determining that a subsequent period of time when the wearable electronic device is being worn based on a subsequent comparison of the motion data and the not-worn profile that specifies the pattern of motion data that is indicative of when the wearable electronic device is not worn by the user; and storing, in the non-transitory machine readable storage medium, data associating the subsequent period of time with a worn state.

What is claimed is:

1. A wearable electronic device to be worn by a user, the wearable electronic device comprising:
   a set of one or more motion sensors to generate motion data samples that represent motion of the wearable electronic device, the motion data samples include a plurality of first motion data samples generated during a first time interval and a plurality of second motion data samples generated during a second time interval;
   a set of one or more processors coupled to the set of motion sensors; and
   a non-transitory machine readable storage medium coupled to the set of one or more processors and having stored therein instructions, which when executed by the set of one or more processors, cause the set of one or more processors to:
obtain the motion data samples generated by the set of motion sensors,
generate a first movement measure based on a combination of the first motion data samples into a single numerical value representative of the motion of the wearable electronic device during the first time interval,
generate a second movement measure based on a combination of the second motion data samples into a single numerical value representative of the motion of the wearable electronic device during the second time interval,
cause the non-transitory machine readable storage medium to store the first movement measure and the second movement measure as time series data,
derive a first feature value corresponding to the first time interval based on the single numerical values of the first and second movement measures,
derive a second feature value corresponding to the second time interval based on at least the single numerical value of the second movement measure,
assign a first sleep state to the user of the wearable electronic device for the first time interval based on the first feature value, and
assign a second sleep state to the user of the wearable electronic device for the second time interval based on the second feature value.

2. The wearable electronic device of claim 1, wherein the instructions, when executed by the set of one or more processors, also cause the set of one or more processors to:
determine levels of activity of the user for each of the first and second time intervals, wherein the determination of the level of activity for the first time interval is based on a comparison of the first feature value with a threshold value, and the levels of activity are used in the assigning of the sleep state.

3. The wearable electronic device of claim 1, wherein the generating of the first and second movement measures is based on a statistical measure of the corresponding motion data samples along an axis of motion of the set of one or more motion sensors.

4. The wearable electronic device of claim 3, wherein each of the statistical measures is one or more of a quantile, an inter-quantile range, a measure of dispersion, and a measure of entropy.

5. The wearable electronic device of claim 3, wherein each of the statistical measures is derived from a frequency domain analysis of the corresponding motion data samples.

6. The wearable electronic device of claim 5, wherein the frequency domain analysis quantifies an amount of periodic motion and compares the amount of periodic motion in two frequency bands.

7. The wearable electronic device of claim 1, wherein the generating of the first and second movements measures is based on a function of a maximum of the motion data and a minimum of the motion data along an axis.

8. The wearable electronic device of claim 7, wherein the function of the maximum motion data and the minimum motion data along the axis comprises application of a weighted value.

9. The wearable electronic device of claim 1, wherein the quantification of the motion data comprises a calculation of a standard deviation of the motion data along an axis.

10. The wearable electronic device of claim 1, wherein the quantification of the motion data comprises a calculation of a temporal derivative of the motion data along an axis.

11. The wearable electronic device of claim 1, wherein the quantification of the motion data comprises a combination of an inter-quantile range of the motion data along an axis.

12. The wearable electronic device of claim 1, wherein the assigning of the sleep state to the user of the wearable electronic device is further based on a plurality of movement measures located within a time window, the plurality of movement measures comprising at least the first and second movement measures, the time window including at least the first and second time intervals.

13. The wearable electronic device of claim 1, wherein the assigning of the sleep state to the user of the wearable electronic device comprises:
assigning a first sleep state to the user of the wearable electronic device for the first time interval based on a first time window including at least the first and second movement measures;
assigning a second sleep state to the user of the wearable electronic device for the second time interval based on a second time window that overlaps with the first time window and includes at least the second movement measure;
consolidating the first and second time intervals into the block of time in response to the first and second sleep states representing a same sleep state of the user.

14. A method executed by a wearable electronic device, the method comprising:
obtaining a plurality of first motion data samples generated by a set of one or more motion sensors, the first motion data samples being generated during a first time interval;
generating a first movement measure based on a combination of the first motion data samples into a single numerical value representative of the motion of the wearable electronic device during the first time interval;
obtaining a plurality of second motion data samples generated by the set of motion sensors, the second motion data samples being generated during a second time interval;
generating a second movement measure based on a combination of the second the motion data samples into a single numerical value representative of the motion of the wearable electronic device during the second time interval;
causing a non-transitory machine readable storage medium to store the first movement measure and the second movement measure as time series data,
deriving a first feature value corresponding to the first time interval based on the single numerical values of the first and second movement measures;
deriving a second feature value corresponding to the second time interval based on at least the single numerical value of the second movement measure;
assigning a first sleep state to a user of the wearable electronic device for the first time interval based on the first feature value, and
assigning a second sleep state to the user of the wearable electronic device for the second time interval based on the second feature value.

15. The method of claim 14, further comprising:
determining levels of activity of the user for each of the first and second time intervals, wherein the determination of the level of activity for the first time interval is based on a comparison of the first feature value with a threshold value, and the levels of activity are used in the assigning of the sleep state.

16. The method of claim 14, wherein the generating of the first and second movement measures is based on a statistical measure of the corresponding motion data samples along an axis of motion of the set of one or more motion sensors.

17. The method of claim 16, wherein each of the statistical measures is one or more of a quantile, an inter-quantile range, a measure of dispersion, and a measure of entropy.

18. The method of claim 16, wherein each of the statistical measures is derived from a frequency domain analysis of the corresponding motion data samples.

19. The method of claim 18, wherein the frequency domain analysis quantifies an amount of periodic motion and compares the amount of periodic motion in two frequency bands.

20. The method of claim 14, wherein the generating of the first and second movements measures is based on a function of a maximum of the motion data and a minimum of the motion data along an axis.

21. A computer readable storage device that includes instructions that, when executed by one or more processors, cause the one or more processors to:
obtain a first movement measure comprising a first single numerical value representative of motion of a wearable device during a first time interval, the first single numerical value being generated based on a combination of a plurality of first motion data samples generated by a set of one or more motion sensors of the wearable electronic device;
obtain a second movement measure comprising a second single numerical value representative of the motion of the wearable device during a second time interval, the second single numerical value being generated based on a combination of a plurality of second motion data samples generated by the motion sensors;
derive a first feature value corresponding to the first time interval based on the single numerical values of the first and second movement measures,
derive a second feature value corresponding to the second time interval based on at least the single numerical value of the second movement measure,
classify a first level of activity of the user for the first time interval based on the first feature value;
classify a second level of activity of the user for the second time interval based on the second feature value;
determine a sleep state for the first time interval based on the first level of activity; and
determine a sleep state for the second time interval based on the second level of activity.

22. The computer readable storage device of claim 21, wherein the instructions, when executed, cause the one or more processors to generate the first single numerical value based on an aggregation of multidimensional acceleration data over the first time interval.

23. The computer readable storage device of claim 21, wherein a device external to and physically separate from the wearable electronic device houses the one or more processors, and the instructions, when executed, cause the one or more processors to obtain the first movement measure and the second movement measure based on a reception of the first movement measure and the second movement measure from the wearable electronic device through a wireless connection.

24. The computer readable storage device of claim 21, wherein the block of time includes time intervals in addition to the first time interval, and the time intervals are classified using a mix of different levels of activity.

* * * * *

UNITED STATES PATENT AND TRADEMARK OFFICE
CERTIFICATE OF CORRECTION

PATENT NO.        : 9,808,185 B2
APPLICATION NO.   : 14/859192
DATED             : November 7, 2017
INVENTOR(S)       : Jacob Antony Arnold It is certified that error appears in the above-identified patent and that said Letters Patent is hereby corrected as shown below:

In the Drawings

Sheet 1 of 19 (FIG. 1) at Line 17 (approx.), Change "varation" to --variation--.

Sheet 15 of 19 (Reference Numeral 1216, FIG. 12) at Line 1, Change "deivce" to --device--.

In the Specification

In Column 10 at Line 30 (approx.), Change "signal" to --signal.--.

In Column 12 at Lines 64-65, Change "timescales" to --timescales.--.

In Column 13 at Lines 19-20, Change "hidden Markov" to --hidden-Markov--.

In Column 24 at Line 10 (approx.), Change "e.g." to --e.g.,--.

In Column 26 at Line 29, Change "800E-800I," to --800F-800I,--.

In the Claims

In Column 44 at Line 45, In Claim 14, after "second" delete "the".

Signed and Sealed this
Tenth Day of April, 2018

Andrei Iancu
*Director of the United States Patent and Trademark Office*